(12) United States Patent
Moon et al.

(10) Patent No.: US 11,987,608 B2
(45) Date of Patent: May 21, 2024

(54) COMPOSITION FOR ACCELERATING CELL PROLIFERATION COMPRISING ERYTHROPOIETIN-DERIVED PEPTIDE

(71) Applicant: SYLUS CO., LTD., Jeollabuk-do (KR)

(72) Inventors: Che Il Moon, Daegu (KR); So Yeon Kim, Daegu (KR); Seung Jun Yoo, Gyeongsangbuk-do (KR); Bong Ki Cho, Daegu (KR)

(73) Assignee: SYLUS CO., LTD., Jeollabuk-do (KR)

( * ) Notice: Subject to any disclaimer, the term of this patent is extended or adjusted under 35 U.S.C. 154(b) by 493 days.

(21) Appl. No.: 17/271,609

(22) PCT Filed: Aug. 21, 2019

(86) PCT No.: PCT/KR2019/010615
§ 371 (c)(1),
(2) Date: Feb. 26, 2021

(87) PCT Pub. No.: WO2020/045886
PCT Pub. Date: Mar. 5, 2020

(65) Prior Publication Data
US 2021/0340206 A1     Nov. 4, 2021

(30) Foreign Application Priority Data
Aug. 27, 2018  (KR) .................. 10-2018-0100580

(51) Int. Cl.
*C07K 14/505* (2006.01)
*A61P 7/06* (2006.01)
*C12N 5/079* (2010.01)
*A61K 38/00* (2006.01)

(52) U.S. Cl.
CPC .............. *C07K 14/505* (2013.01); *A61P 7/06* (2018.01); *C12N 5/0618* (2013.01); *A61K 38/00* (2013.01); *C12N 2501/14* (2013.01)

(58) Field of Classification Search
CPC ........... C07K 14/505; C07K 7/08; A61P 7/06; C12N 5/0618; C12N 2501/14; C12N 5/0647; A61K 38/00; A23L 33/18; A23V 2002/00

See application file for complete search history.

(56) References Cited

U.S. PATENT DOCUMENTS

| 10,385,127 B2 | 8/2019 | Ghosh et al. | |
|---|---|---|---|
| 2009/0197801 A1* | 8/2009 | Berezin .................. | A61K 38/07 435/375 |
| 2010/0081786 A1 | 4/2010 | Danishefsky et al. | |
| 2014/0378378 A1 | 12/2014 | Kim | |
| 2016/0168199 A1 | 6/2016 | Brines et al. | |
| 2019/0017027 A1 | 1/2019 | Lanza et al. | |
| 2020/0407410 A1 | 12/2020 | Moon et al. | |

FOREIGN PATENT DOCUMENTS

| KR | 101148191 | 5/2012 |
|---|---|---|
| KR | 20150090101 | 8/2015 |
| KR | 20160052537 | 5/2016 |
| KR | 20170102040 | 9/2017 |
| KR | 20180099546 | 9/2018 |
| WO | 0219963 | 3/2002 |
| WO | 2006119767 | 11/2006 |
| WO | 2007120614 | 10/2007 |
| WO | 2009094172 | 7/2009 |
| WO | 2010115141 | 10/2010 |
| WO | 2018155997 | 8/2018 |

OTHER PUBLICATIONS

Thermofischer, Peptide design, published on line 2011.*
Uniprot Protein Database, protein Accession B7ZKK5, accessed on Jul. 11, 2023.*
Fabiana Busti, Anemia and Iron Deficiency in Cancer Patients: Role of Iron Replacement Therapy, Pharmaceuticals 2018, 11, 94.*
"Search Report of Europe Counterpart Application", dated May 2, 2022, p. 1-p. 8.
"International Search Report (Form PCT/ISA/210) of PCT/KR2019/010615," dated Nov. 25, 2019, with English translation thereof, pp. 1-5.
Seung-Jun Yoo, et al., "Neuroprotective Effects of an Erythropoietin-Derived Peptide in PC12 Cells under Oxidative Stress," CNS & neurological disorders drug targets, Aug. 2016, vol. 15, pp. 927-934.
Seung-Jun Yoo, et al., "The erythropoietin-derived peptide MK-X and erythropoietin have neuroprotective effects against ischemic brain damage," Cell Death & Disease, vol. 8, Aug. 2017, pp. 1-13.

* cited by examiner

*Primary Examiner* — Julie Ha
*Assistant Examiner* — Erinne R Dabkowski
(74) *Attorney, Agent, or Firm* — JCIPRNET

(57) ABSTRACT

Provided is a composition for accelerating cell proliferation, including an erythropoietin-derived peptide as an active ingredient. Due to having a simpler structure than that of the existing natural human erythropoietin, the composition easily passes through the tissue-blood barrier, exhibits excellent cell protective activity, does not cause side effects of cell proliferation, and improves a hematopoietic function. Accordingly, the composition is used in the treatment or prevention of an anemic disorder.

10 Claims, 25 Drawing Sheets

Specification includes a Sequence Listing.

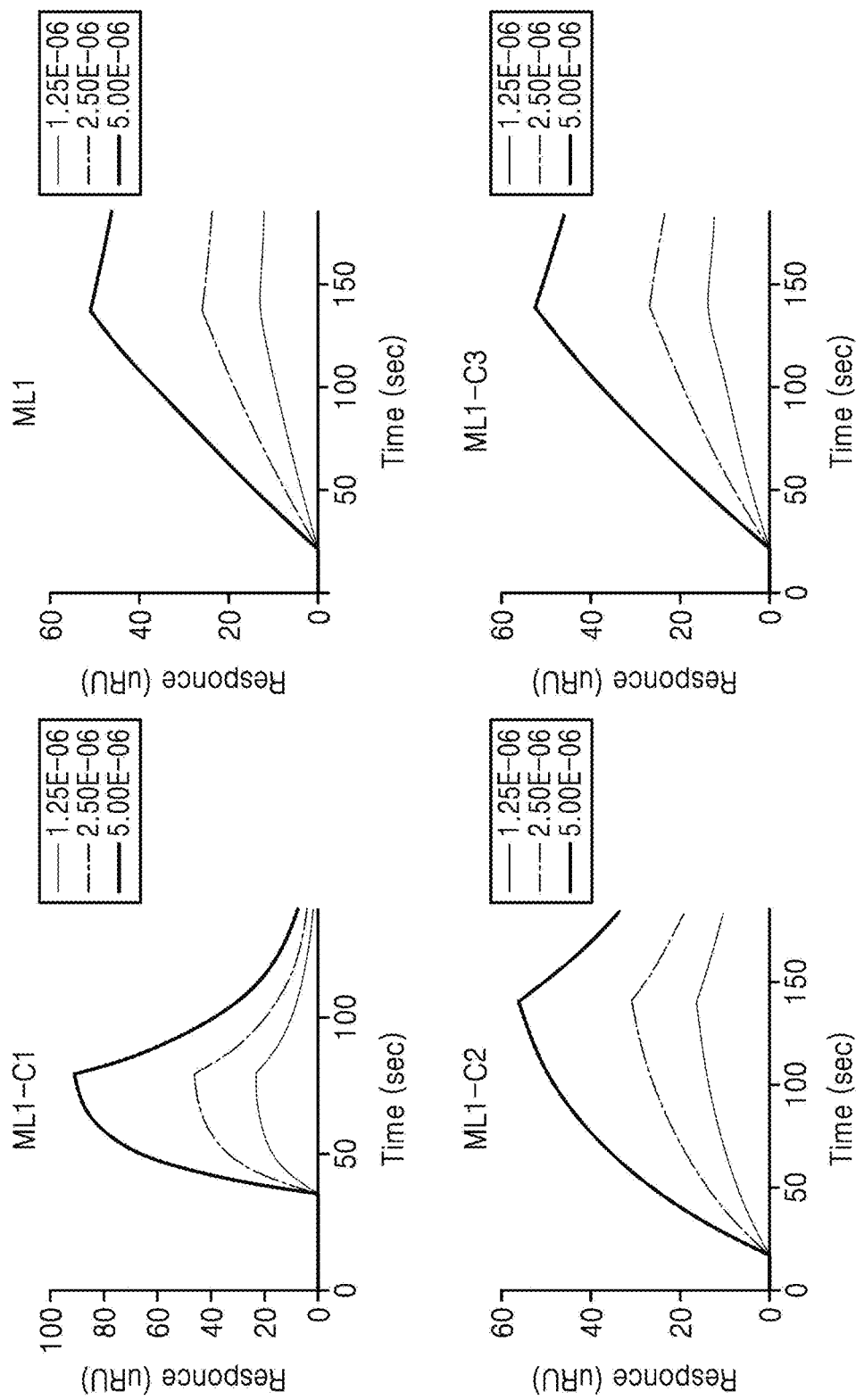

SEQUENCE LISTING

```
<160> NUMBER OF SEQ ID NOS: 28

<210> SEQ ID NO 1
<211> LENGTH: 23
<212> TYPE: PRT
<213> ORGANISM: Artificial Sequence
<220> FEATURE:
<223> OTHER INFORMATION: ML1

<400> SEQUENCE: 1

Leu Gln Leu His Val Asp Lys Ala Val Ser Gly Leu Arg Ser Leu Thr
1               5                   10                  15

Thr Leu Leu Arg Ala Leu Gly
            20

<210> SEQ ID NO 2
<211> LENGTH: 20
<212> TYPE: PRT
<213> ORGANISM: Artificial Sequence
<220> FEATURE:
<223> OTHER INFORMATION: ML2

<400> SEQUENCE: 2

Leu His Val Asp Lys Ala Val Ser Gly Leu Arg Ser Leu Thr Thr Leu
1               5                   10                  15

Leu Arg Ala Leu
            20

<210> SEQ ID NO 3
<211> LENGTH: 10
<212> TYPE: PRT
<213> ORGANISM: Artificial Sequence
<220> FEATURE:
<223> OTHER INFORMATION: ML3

<400> SEQUENCE: 3

Thr Lys Val Asn Phe Tyr Ala Trp Lys Arg
1               5                   10

<210> SEQ ID NO 4
<211> LENGTH: 24
<212> TYPE: PRT
<213> ORGANISM: Artificial Sequence
<220> FEATURE:
<223> OTHER INFORMATION: ML4

<400> SEQUENCE: 4

Asp Lys Ala Val Ser Gly Leu Arg Ser Leu Thr Thr Leu Leu Arg Ala
1               5                   10                  15
```

Leu Gly Ala Gln Lys Glu Ala Ile
            20

<210> SEQ ID NO 5
<211> LENGTH: 14
<212> TYPE: PRT
<213> ORGANISM: Artificial Sequence
<220> FEATURE:
<223> OTHER INFORMATION: ML5

<400> SEQUENCE: 5

Ser Gly Leu Arg Ser Leu Thr Thr Leu Leu Arg Ala Leu Gly
1               5                   10

<210> SEQ ID NO 6
<211> LENGTH: 20
<212> TYPE: PRT
<213> ORGANISM: Artificial Sequence
<220> FEATURE:
<223> OTHER INFORMATION: ML6

<400> SEQUENCE: 6

Ser Gly Leu Arg Ser Leu Thr Thr Leu Leu Arg Ala Leu Gly Ala Gln
1               5                   10                  15

Lys Glu Ala Ile
            20

<210> SEQ ID NO 7
<211> LENGTH: 25
<212> TYPE: PRT
<213> ORGANISM: Artificial Sequence
<220> FEATURE:
<223> OTHER INFORMATION: ML7

<400> SEQUENCE: 7

Trp Glu Pro Leu Gln Leu His Val Asp Lys Ala Val Ser Gly Leu Arg
1               5                   10                  15

Ser Leu Thr Thr Leu Leu Arg Ala Leu
            20                  25

<210> SEQ ID NO 8
<211> LENGTH: 17
<212> TYPE: PRT
<213> ORGANISM: Artificial Sequence
<220> FEATURE:
<223> OTHER INFORMATION: ML8

<400> SEQUENCE: 8

Asp Lys Ala Val Ser Gly Leu Arg Ser Leu Thr Thr Leu Leu Arg Ala
1               5                   10                  15

Leu

<210> SEQ ID NO 9
<211> LENGTH: 23
<212> TYPE: PRT
<213> ORGANISM: Artificial Sequence
<220> FEATURE:
<223> OTHER INFORMATION: ML1-1

<400> SEQUENCE: 9

Leu Gln Leu His Val Leu Lys Arg Val Ser Gly Leu Leu Ser His Thr
1               5                   10                  15

Met Leu Leu Lys Ala Leu Gly
            20

```
<210> SEQ ID NO 10
<211> LENGTH: 20
<212> TYPE: PRT
<213> ORGANISM: Artificial Sequence
<220> FEATURE:
<223> OTHER INFORMATION: ML2-1

<400> SEQUENCE: 10

Arg His Val Gln Lys Ala Glu Ser Gly Leu Arg Ser Leu Thr Lys Leu
1               5                   10                  15

Leu Arg Glu Leu
            20

<210> SEQ ID NO 11
<211> LENGTH: 10
<212> TYPE: PRT
<213> ORGANISM: Artificial Sequence
<220> FEATURE:
<223> OTHER INFORMATION: ML3-1

<400> SEQUENCE: 11

Thr Arg Val Asn Tyr Gln Ala Trp Lys Arg
1               5                   10

<210> SEQ ID NO 12
<211> LENGTH: 24
<212> TYPE: PRT
<213> ORGANISM: Artificial Sequence
<220> FEATURE:
<223> OTHER INFORMATION: ML4-1

<400> SEQUENCE: 12

Lys Lys Ala Val Ser Gly Leu Lys Thr Leu Thr His Ile Leu Arg Ala
1               5                   10                  15

Leu Gly Ala Gln Lys Glu Ala Ile
            20

<210> SEQ ID NO 13
<211> LENGTH: 14
<212> TYPE: PRT
<213> ORGANISM: Artificial Sequence
<220> FEATURE:
<223> OTHER INFORMATION: ML5-1

<400> SEQUENCE: 13

Ala Gly Leu Arg Ser Arg Ala His Leu Arg Arg Ala Leu Ala
1               5                   10

<210> SEQ ID NO 14
<211> LENGTH: 20
<212> TYPE: PRT
<213> ORGANISM: Artificial Sequence
<220> FEATURE:
<223> OTHER INFORMATION: ML6-1

<400> SEQUENCE: 14

Lys Gly Leu Arg Ser Leu Ile Ser Leu Leu Arg Ala Leu Gly Ala Gln
1               5                   10                  15

Lys Glu Ala Ile
            20

<210> SEQ ID NO 15
<211> LENGTH: 25
<212> TYPE: PRT
<213> ORGANISM: Artificial Sequence
```

```
<220> FEATURE:
<223> OTHER INFORMATION: ML7-1

<400> SEQUENCE: 15

Asp Glu Ala Leu Asp Leu Glu Val Asp Lys Ala Ala Thr Gly Leu Arg
1               5                   10                  15

Thr Leu Thr Thr Leu Ile Arg Ala Leu
            20                  25

<210> SEQ ID NO 16
<211> LENGTH: 13
<212> TYPE: PRT
<213> ORGANISM: Artificial Sequence
<220> FEATURE:
<223> OTHER INFORMATION: ML8-1

<400> SEQUENCE: 16

Asn Lys Ala Val Ala Gly Leu Arg Ser Leu Thr Val Asn
1               5                   10

<210> SEQ ID NO 17
<211> LENGTH: 23
<212> TYPE: PRT
<213> ORGANISM: Artificial Sequence
<220> FEATURE:
<223> OTHER INFORMATION: ML1-H1

<400> SEQUENCE: 17

Leu Gln Leu His Val Leu Lys Ala Val Ser Gly Leu Leu Thr His Thr
1               5                   10                  15

Thr Leu Leu Lys Ala Leu Gly
            20

<210> SEQ ID NO 18
<211> LENGTH: 23
<212> TYPE: PRT
<213> ORGANISM: Artificial Sequence
<220> FEATURE:
<223> OTHER INFORMATION: ML1-H2

<400> SEQUENCE: 18

Leu Gln Leu His Val Leu Lys Ala Val Ser Gly Leu Leu Thr Leu Thr
1               5                   10                  15

Met Ile Arg Arg Ala Leu Gly
            20

<210> SEQ ID NO 19
<211> LENGTH: 23
<212> TYPE: PRT
<213> ORGANISM: Artificial Sequence
<220> FEATURE:
<223> OTHER INFORMATION: ML1-H3

<400> SEQUENCE: 19

Leu Gln Leu His Val Leu Lys Ala Val Ala Gly Leu Arg Thr Leu Ala
1               5                   10                  15

Met Ile Arg Arg Ala Leu Ala
            20

<210> SEQ ID NO 20
<211> LENGTH: 23
<212> TYPE: PRT
<213> ORGANISM: Artificial Sequence
<220> FEATURE:
<223> OTHER INFORMATION: ML1-C1
```

```
<400> SEQUENCE: 20

Leu Asp Leu Glu Val Asp Lys Ala Val Ser Gly Leu Arg Ser Leu Thr
1               5                   10                  15

Thr Leu Leu Arg Ala Leu Gly
            20

<210> SEQ ID NO 21
<211> LENGTH: 23
<212> TYPE: PRT
<213> ORGANISM: Artificial Sequence
<220> FEATURE:
<223> OTHER INFORMATION: ML1-C2

<400> SEQUENCE: 21

Leu Gln Arg His Val Asp Lys Arg Val Ser Gly Leu Arg Ser Leu Thr
1               5                   10                  15

Thr Leu Leu Arg Ala Leu Gly
            20

<210> SEQ ID NO 22
<211> LENGTH: 23
<212> TYPE: PRT
<213> ORGANISM: Artificial Sequence
<220> FEATURE:
<223> OTHER INFORMATION: ML1-C3

<400> SEQUENCE: 22

Leu Gln Arg His Val Lys Lys Arg Val Lys Gly Leu Lys Ser Leu Thr
1               5                   10                  15

Thr Leu Leu Arg Ala Leu Gly
            20

<210> SEQ ID NO 23
<211> LENGTH: 16
<212> TYPE: PRT
<213> ORGANISM: Artificial Sequence
<220> FEATURE:
<223> OTHER INFORMATION: ML1-L2

<400> SEQUENCE: 23

Leu His Val Asp Lys Ala Val Ser Gly Leu Arg Ser Leu Thr Thr Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: ML1-K2

<400> SEQUENCE: 24

Lys His Val Asp Lys Ala Val Ser Gly Leu Arg Ser Leu Thr Thr Lys
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: ML1-R2

<400> SEQUENCE: 25

Arg His Val Asp Lys Ala Val Ser Gly Leu Arg Ser Leu Thr Thr Arg
1               5                   10                  15
```

```
<210> SEQ ID NO 26
<211> LENGTH: 19
<212> TYPE: PRT
<213> ORGANISM: Artificial Sequence
<220> FEATURE:
<223> OTHER INFORMATION: MLP

<400> SEQUENCE: 26

Leu His Val Asp Lys Ala Val Ser Gly Leu Arg Ser Leu Thr Thr Leu
1               5                   10                  15

Leu Arg Ala

<210> SEQ ID NO 27
<211> LENGTH: 19
<212> TYPE: PRT
<213> ORGANISM: Artificial Sequence
<220> FEATURE:
<223> OTHER INFORMATION: MLP-C

<400> SEQUENCE: 27

Arg His Val Lys Lys Arg Val Lys Gly Leu Lys Ser Leu Thr Thr Leu
1               5                   10                  15

Leu Arg Ala

<210> SEQ ID NO 28
<211> LENGTH: 19
<212> TYPE: PRT
<213> ORGANISM: Artificial Sequence
<220> FEATURE:
<223> OTHER INFORMATION: MLP-H

<400> SEQUENCE: 28

Leu His Val Leu Lys Ala Val Ser Gly Leu Leu Thr Leu Thr Met Ile
1               5                   10                  15

Arg Arg Ala
```

COMPOSITION FOR ACCELERATING CELL PROLIFERATION COMPRISING ERYTHROPOIETIN-DERIVED PEPTIDE

CROSS-REFERENCE TO RELATED APPLICATION

This application is a 371 application of the International PCT application serial no. PCT/KR2019/010615 filed on Aug. 21, 2019, which claims the priority benefits of Korean Patent Application No. 10-2018-0100580, filed on Aug. 27, 2018. The entirety of each of the above-mentioned patent applications is hereby incorporated by reference herein and made a part of this specification.

TECHNICAL FIELD

The present application claims the benefit of Korean Patent Application No. 10-2018-0100580, filed on Aug. 27, 2018, in the Korean Intellectual Property Office, and the entire disclosure of the above specification is incorporated by reference in the present application.

The present disclosure relates to a composition for accelerating cell proliferation, comprising an erythropoietin-derived peptide as an active ingredient.

BACKGROUND ART

During lifetime, the human body is consistently exposed to stimuli, which are harmful to the human body, and in response to such exposure, the individual protects their body. Harmful stimuli include various stimuli such as hypoxia, infection, mechanical stimulations, etc., and defense mechanisms against such stimuli exist at a cellular level. Various cytokines that are secreted as a defense mechanism against stimuli play a role in protecting an individual by killing abnormal cells produced due to exposure to stimuli or by preventing death of normal cells.

Erythropoietin is a glycoprotein having a molecular weight of about 30,000, and is a hematopoietic cytokine which promotes differentiation of cells forming red blood cells and increases the number of red blood cells to exhibit an effect of preventing or ameliorating anemia. This protein initiates its action by binding to a receptor of red blood cell precursors and induces an increase in intracellular calcium ions, an increase in DNA biosynthesis, stimulation of hemoglobin production, etc. Therefore, erythropoietin may be used as a therapeutic agent for anemia, such as anemia in patients with a kidney disease, anemia in premature babies, anemia associated with hypothyroidism, anemia associated with malnutrition, anemia associated with chronic renal failure, postoperative anemia, etc.

Erythropoietin artificially prepared by cell culture or synthesis exhibits satisfactory activity in terms of cell protective effects and cell proliferative effects, but has a relatively short half-life. To address the foregoing issues, erythropoietin variants with an increased half-life were developed through darbopoetin alfa and methoxypolyethylene glycol-epoetin beta, and have been in use as anemia drugs. However, these drugs have difficulty of drug delivery in some tissues with the tissue-blood barrier, such as brain tissues. To overcome such shortcomings, peptides having a small size, produced by artificially synthesizing a portion of erythropoietin, have been developed; however, these peptides only have tissue protective effects, without cell proliferative effects, and thus are effective for neurological disorders and the like, but have limitations as drugs for anemia and other diseases that require cell proliferative effects.

DESCRIPTION OF EMBODIMENTS

Technical Problem

Provided is a peptide, which is described by one or more amino acid sequence selected from SEQ ID NOs: 26 to 28.

Provided is a composition for accelerating proliferation or differentiation of cells, which comprises, as an active ingredient, one or more peptides selected from SEQ ID NOs: 1 to 28.

Provided is a composition for improving a hematopoietic function, which comprises, as an active ingredient, one or more peptides selected from SEQ ID NOs: 1 to 28.

Provided is a pharmaceutical composition for preventing or treating an anemic disorder, which comprises, as an active ingredient, one or more peptides selected from SEQ ID NOs: 1 to 28.

Provided is a health functional food composition for preventing or ameliorating an anemic disorder, which comprises, as an active ingredient, one or more peptides selected from SEQ ID NOs: 1 to 28.

Provided is a pharmaceutical composition for preventing or treating a hematopoietic disorder, which comprises, as an active ingredient, one or more peptides selected from SEQ ID NOs: 1 to 28.

Provided is a health functional food composition for preventing or ameliorating a hematopoietic disorder, which comprises, as an active ingredient, one or more peptides selected from SEQ ID NOs: 1 to 28.

Provided is a method for treating an anemic disorder, comprising a step of administering, to a subject in need thereof, a therapeutically effective amount of a composition comprising, as an active ingredient, one or more peptides selected from SEQ ID NOs: 1 to 28.

Provided is a method for treating a hematopoietic disorder, comprising a step of administering, to a subject in need thereof, a therapeutically effective amount of a composition comprising, as an active ingredient, one or more peptides selected from SEQ ID NOs: 1 to 28.

Provided is a use of a composition comprising one or more peptides selected from SEQ ID NOs: 1 to 28, in the preparation of a therapeutic agent for the treatment of an anemic disorder.

Provided is a use of a composition comprising one or more peptides selected from SEQ ID NOs: 1 to 28, in the preparation of a therapeutic agent for the treatment of a hematopoietic disorder.

Solution to Problem

An aspect provides a peptide described by one or more sequences selected from SEQ ID NOs: 26 to 28. The peptide may be derived from an erythropoietin protein sequence. The peptide may bind to an erythropoietin receptor. For example, the peptide may bind to a target site 1 or a target site 2 of the receptor.

Another aspect provides a composition for accelerating proliferation or differentiation of cells, comprising, as an active ingredient, one or more peptides selected from SEQ ID NOs: 1 to 28. Further provided is a composition for accelerating proliferation or differentiation of cells, comprising, as an active ingredient, one or more peptides selected from SEQ ID NOs: 20 to 22, and 27. The peptide may be derived from an erythropoietin protein sequence, and the peptide may be derived from an erythropoietin binding site. The peptide is characterized by having a binding affinity of 0.1 µM to 1 nM to an erythropoietin receptor. In detail, the erythropoietin receptor has two target sites, through which the erythropoietin receptor forms a complex with erythropoietin, and it is known that of the two binding target sites, the target site 1 forms a strong bond (KD=up to 1 nM) and the target site 2 forms a weak bond (KD=up to 1 µM). A peptide according to one embodiment may regulate cell proliferative effects by forming a weak bond with the target site 2 of the erythropoietin receptor.

The peptide may form an alpha-helical structure and may have cell protective activity. Further, the peptide may accelerate proliferation or differentiation of hemocytoblasts, fat cells, pancreatic cells, muscle cells, blood vessel cells, or skin cells.

The term "hemocytoblasts" as used in the present specification is also referred to as hematopoietic stem cells and refers to cells that perform the hematopoiesis through self-renewal and differentiation. Hemocytoblasts undergo intermediate stages of various blood cells, which are precursor cells, to finally mature to terminal cells, and differentiate to various cells in blood, such as red blood cells, platelets, neutrophils, eosinophils, basophils, monocytes, T cells, B cells, natural killer cells, or dendritic cells, and thus, the development of red blood cells or lymphocytes may be accelerated by differentiation of such hemocytoblasts. Accordingly, the composition according to an embodiment may be used as a therapeutic agent for anemia by accelerating proliferation or differentiation of hemocytoblasts. Further, the composition induces proliferation or differentiation of cells in tissues expressing an erythropoietin receptor, such as fat tissues, pancreas, muscles, blood vessels, and skin, and thus may be used in the prevention or treatment of conditions that require cell proliferative effects, such as obesity, diabetes, muscle regeneration, blood vessel regeneration, skin regeneration, and the like.

Another aspect provides a composition for improving a hematopoietic function, comprising, as an active ingredient, one or more peptides selected from SEQ ID NOs: 1 to 28. Specific details about the peptide are as described above. The composition improves a hematopoietic function to thereby treat or ameliorate anemia, erythrocytopenia, or hematopoiesis, enhances an overall hematopoietic activity of a body, and accelerates regeneration of muscles, blood vessels, and skin, and inhibits obesity to thereby provide benefits in enhancing physical strength and maintaining health.

Another aspect provides a composition for preventing or treating an anemic disorder, comprising, as an active ingredient, one or more peptides selected from SEQ ID NOs: 1 to 28. Further, provided is a method for preventing or treating an anemic disorder, comprising a step in which a pharmaceutically effective amount of the composition is administered to a subject in need thereof, is brought in contact with cells in vitro, or administered in vivo to a test animal. Specific details about the peptide are as described above.

The term "anemia" as used in the present specification, refers to any condition related to a decrease in the amount of red blood cells or hemoglobin in red blood cells below a normal level, and refers to any condition related to a failure to produce healthy red blood cells, or any condition in which the rate at which red blood cells are being produced is insufficient due to loss or destruction of too large a number of red blood cells.

The composition accelerates development of red blood cells or lymphocytes by accelerating proliferation or differentiation of hemocytoblasts, and thus may be used in the prevention or treatment of an anemic disorder. The anemic disorder may be, for example, acute or chronic anemia, anemia associated with a kidney disorder, anemia associated with kidney failure, anemia associated with hemopathy, radiation therapy-induced anemia, chemotherapy-induced anemia, anemia associated with a surgical procedure, anemia associated with an infection, anemia associated with nutritional deficiency, abnormal erythropoiesis, initial anemia associated with premature birth, or a combination thereof.

The composition according to a specific embodiment may comprise, with respect to the total weight of the composition, 0.001 wt % to 80 wt % of one or more peptides selected from SEQ ID NOs: 1 to 28. An administration dose of the composition may be 0.01 mg to 10,000 mg, 0.1 mg to 1000 mg, 1 mg to 100 mg, 0.01 mg to 1,000 mg, 0.01 mg to 100 mg, 0.01 mg to 10 mg, or 0.01 mg to 1 mg. However, the administration dose may be prescribed in various amounts depending on a number of factors, i.e., a preparation method, a manner of administration, a patient's age, body weight, sex, severity of the disease, diet, administration time, administration route, rate of excretion, and reactive sensitivity, and the administration dose may be appropriately selected by those skilled in the art by taking into consideration such factors. In terms of administration frequency, the administration may be made once, or within a range of clinically acceptable side effects, may be made twice or more, and also, in terms of administration site, the administration may be made at one site, or at two or more sites. Further, for non-human animals, the administration may be made at the same administration dose per kg as a human, or alternatively for example, may be made at a dose that is converted from the above administration dose by using the volume ratio (for example, a mean value) of an organ (e.g., heart) between a target animal and the human. Possible administration routes may include oral, subglossal, non-oral (for example, subcutaneous, intramuscular, intra-arterial, intraperitoneal, intradural or intravenous), rectal, local (including percutaneous) routes, inhalation, and injection, or may include insertion of a material or an implantable device. An animal to be treated according to a specific embodiment may be a human and any other desired mammal, and more specifically, includes a human, a monkey, a mouse, a rat, a rabbit, a sheep, a cow, a dog, a horse, a pig, and the like.

A pharmaceutical composition according to a specific embodiment may comprise a pharmaceutically acceptable carrier and/or an additive. For example, the pharmaceutical composition may comprise sterile water, a physiological saline, a known buffer (phosphoric acid, citric acid, and other organic acids, etc.), a stabilizer, a salt, an antioxidant (e.g. ascorbic acid), a surfactant, a suspension, an isotonic agent, or a preservative. For local administrations, the pharmaceutical composition may be combined with an organic material such as a biopolymer, or an inorganic material such as hydroxyapatite, and more specifically, may include a combination with a collagen matrix, a polylactic acid complex or copolymer, a polyethyleneglycol polymer or copolymer, or chemical derivatives thereof, or the like. In a case in which the pharmaceutical composition according to a specific embodiment is prepared into a formulation suitable for injection, the peptide may be dissolved in a pharmaceutically acceptable carrier, or may be dissolved and frozen in a solution state.

The pharmaceutical composition according to a specific embodiment, if needed for its mode of administration or formulation, may appropriately include a suspension, a solubilizing agent, a stabilizing agent, an isotonic agent, a preservative, an anti-adhesion agent, a surfactant, a diluent, an excipient, a pH adjustment agent, a pain-reducing agent, a buffer, a reducing agent, an antioxidant, or the like. In addition to the examples disclosed above, pharmaceutically acceptable carriers and agents suitable for the present disclosure are disclosed in detail in literature [Remington's Pharmaceutical Sciences, 19th ed., 1995]. The pharmaceutical composition according to a specific embodiment may be formulated using a pharmaceutically acceptable carrier and/or an excipient and prepared as a unit dosage form, or may be injected and prepared in a multi-dose container, according to a method that can be easily enabled by a person skilled in the art in the technical field to which the present disclosure belongs. In detail, the formulation may be an oil, a solution in aqueous medium, a suspension, or an emulsion, or may be in a form of powder, granules, pills, or capsules.

Another aspect provides a health functional food composition for preventing or ameliorating an anemic disorder, comprising, as an active ingredient, one or more peptides selected from SEQ ID NOs: 1 to 28. Specific details about the above peptide are as described above.

The health food composition may be used in combination with other food or food ingredients other than the peptide, and may be appropriately used according to a known method. A mixing amount of an active ingredient may be appropriately determined in accordance with an intended purpose of use (prevention, health, or therapeutic treatment). In general, in the preparation of a health functional food, the composition of the present specification may be added in an amount of 15 parts by weight or less with respect to raw materials. The type of the health functional food is not particularly limited.

Another aspect provides a pharmaceutical composition for preventing or ameliorating a hematopoietic disorder, comprising, as an active ingredient, one or more peptides selected from SEQ ID NOs: 1 to 28. Further provided is a method for preventing or treating a hematopoietic disorder, comprising a step in which a pharmaceutically effective amount of the composition is administered to a subject in need thereof, or brought in contact with cells in vitro, or administered in vivo to a test animal.

Another aspect provides a health functional food composition for preventing or ameliorating a hematopoietic disorder, comprising, as an active ingredient, one or more peptides selected from SEQ ID NOs: 1 to 28. Specific details about the above peptide are as described above.

The term "hematopoietic disorder" as used in the present specification refers to any condition related to a failure of normal blood cell production due to defective hematopoiesis, and the hematopoietic disorder may cause various diseases. In detail, such diseases may be aplastic anemia, leukemia or lymphoma, chronic liver disease, kidney failure, severe infection, bone marrow disorder-type thrombocytopenia, idiopathic thrombocytopenic purpura (ITP), thrombasthenia, lymphopenia, neutropenia, monocytopenia, granulocytopenia, myelodysplastic syndrome, or myeloproliferative disease.

As described above, an erythropoietin-derived peptide according to an aspect accelerates proliferation or differentiation of cells, and not only has cell protective effects on damaged cells, but also exhibits hematopoietic effects, and thus, may be used in the treatment or prevention of various conditions that give rise to an anemic disorder and a hematopoietic disorder. Further, the peptide induces proliferation or differentiation of cells in tissues expressing an erythropoietin receptor, such as fat tissues, pancreas, muscles, blood vessels, and skin, and thus may be used in the prevention or treatment of a condition that requires cell proliferative effects, such as obesity, diabetes, muscle regeneration, blood vessel regeneration, skin regeneration, and the like.

Advantageous Effects of Disclosure

A composition according to an aspect comprises a peptide derived from an erythropoietin protein sequence, and due to having a simpler structure, as compared with the existing natural human erythropoietin, easily passes through a tissue-blood barrier, exhibits excellent cell protective activity, has no side effect of cell proliferation, and can improve a hematopoietic function, and thus can be used in the treatment or prevention of an anemic disorder. Further, the composition is economically advantageous due to its low production cost, and thus may be utilized as an alternative material to erythropoietin, that can be easily delivered to tissues in vivo and has cell proliferative effects.

BRIEF DESCRIPTION OF DRAWINGS

FIGS. 2A-2C are graphs showing binding strength as confirmed by the SPR technique to confirm whether an erythropoietin-derived peptide is able to act on an erythropoietin receptor.

MODE OF DISCLOSURE

Figure 1:
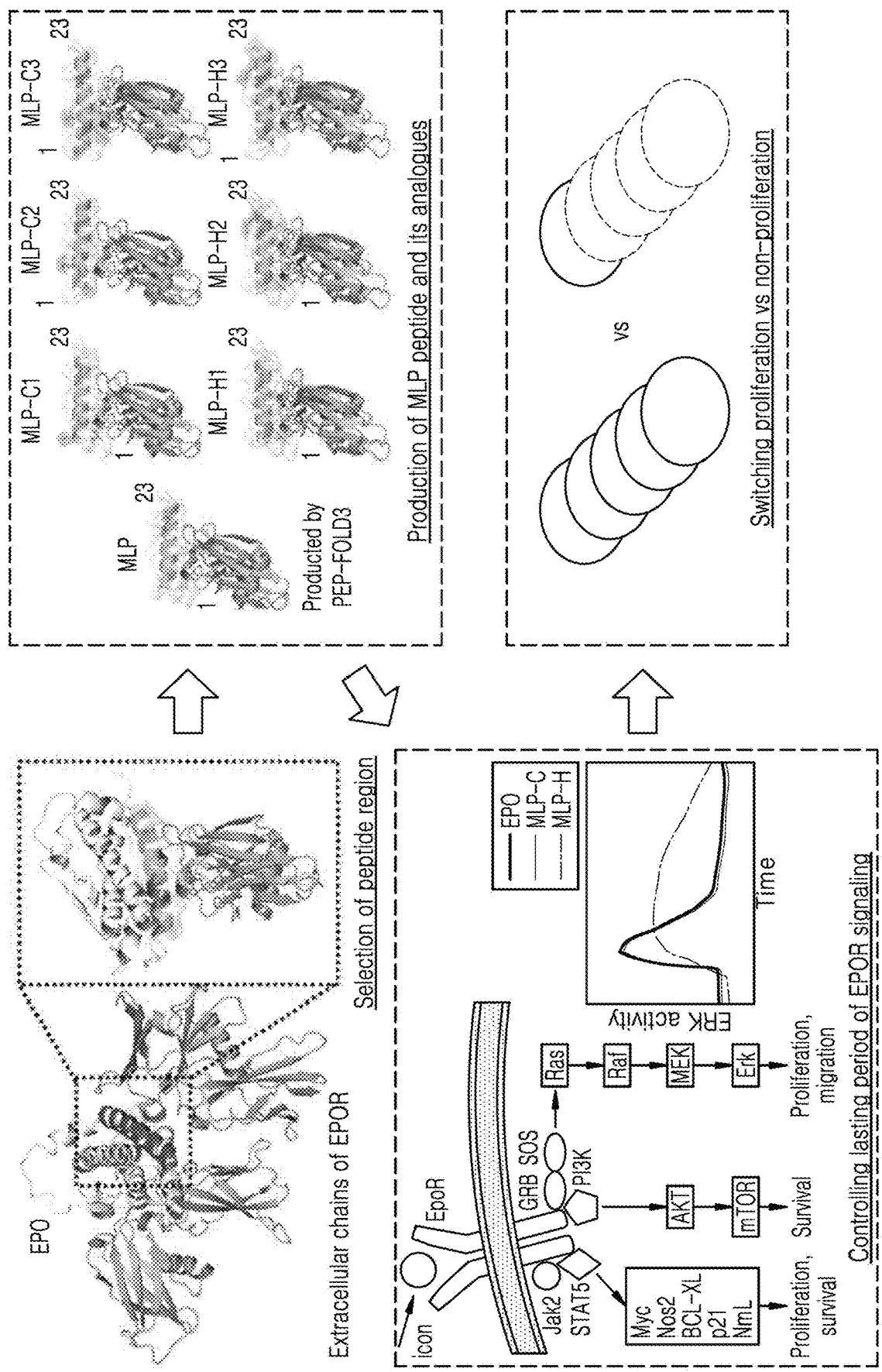
FIG. 1 is a diagram representing an erythropoietin-derived peptide according to one embodiment and analogues thereof.

Hereinbelow, preferred embodiments are provided to help understanding of the present disclosure. However, as the embodiments disclosed below are provided merely to help understanding of the present disclosure, the scope of the present disclosure is not limited by the embodiments disclosed below.

EXAMPLES

Example 1. Synthesis of Erythropoietin-Derived Peptides

Erythropoietin-derived peptides of the present disclosure were synthesized as monomers according to a known solid phase peptide synthesis technology (Peptron, Daejeon, Korea).

In detail, erythropoietin-derived peptides, which are able to bind to crucial amino acid sequences (Arg103, Ser104, Leu105, Leu108, and Arg110) in a sequence of a target site (site 2) of the natural erythropoietin receptor were synthesized, and specific characteristics of the peptides were examined, respectively. To measure concentrations of the synthesized peptides, liquid chromatography/mass-selective detector (HP 1100 series) was used. Purity was measured by high performance liquid chromatography (SHIMADZU prominence HPLC) analysis (>95% purity). The erythropoietin-derived peptides are shown in Table 1 below.

TABLE 1

| Peptide Name | Sequence | SEQ ID NO |
|---|---|---|
| ML1 | LQLHVDKAVSGLRSLTTLLRALG | 1 |
| ML2 | LHVDKAVSGLRSLTTLLRAL | 2 |
| ML3 | TKVNFYAWKR | 3 |
| ML4 | DKAVSGLRSLTTLLRALGAQKEAI | 4 |
| ML5 | SGLRSLTTLLRALG | 5 |
| ML6 | SGLRSLTTLLRALGAQKEAI | 6 |
| ML7 | WEPLQLHVDKAVSGLRSLTTLLRAL | 7 |
| ML8 | DKAVSGLRSLTTLLRAL | 8 |
| ML1-1 | LQLHVLKRVSGLLSHTMLLKALG | 9 |
| ML2-1 | RHVQKAESGLRSLTKLLREL | 10 |
| ML3-1 | TRVNYQAWKR | 11 |
| ML4-1 | KKAVSGLKTLTHILRALGAQKEAI | 12 |
| ML5-1 | AGLRSRAHLRRALA | 13 |
| ML6-1 | KGLRSLISLLRALGAQKEAI | 14 |
| ML7-1 | DEALDLEVDKAATGLRTLTTLIRAL | 15 |
| ML8-1 | NKAVAGLRSLTVN | 16 |

Hydrophobicity, charge, and isoelectric point (pI) of the erythropoietin-derived peptides, ML1-1, ML2-1, ML3-1, ML4-1, ML5-1, ML6-1, ML7-1, and ML8-1 were calculated and are shown in Table 2 below.

TABLE 2

| Peptide Name | Hydrophobicity | Charge (pH 7) | pI | Target Site |
|---|---|---|---|---|
| ML1-1 | 8.25 | 3.4 | 11.2 | 2 |
| ML2-1 | −4.45 | 3.2 | 10.94 | 2 |
| ML3-1 | −10.07 | 2.9 | 10.94 | 1 |
| ML4-1 | 5 | 6.1 | 11.41 | 2 |
| ML5-1 | −4.15 | 4.1 | 12.48 | 2 |
| ML6-1 | 8.85 | 2.9 | 10.94 | 2 |
| ML7-1 | 2.05 | −2.1 | 4.59 | 2 |
| ML8-1 | 5.7 | 1.9 | 11.12 | 2 |

Example 2. Erythropoietin-Derived Peptides Using Partial Sequence (1)

For sequence modification experiments, a binding model of erythropoietin and its receptor was based on a previously known binding structure (Protein Data Bank ID: 1EER). Based on known characteristics of amino acids, amino acids of the erythropoietin-derived peptides were substituted. Amino acids are classified into 4 types (① non-polar or hydrophobic, ② neutral, ③ negatively charged, and ④ positively charged) according to polarity of their side chains. Based on information of non-polar (hydrophobic), neutral, negatively charged, or positively charged amino acids, the existing amino acid sequences were substituted to induce modification in respective characteristics.

Peptides prepared by partially modifying sequences of ML1 peptide and their characteristics are shown in Tables 3 and 4.

TABLE 3

| Peptide Name | Sequence | SEQ ID NO |
|---|---|---|
| ML1 | LQLHVDKAVSGLRSLTTLLRALG | 1 |
| ML1-H1 | LQLHVLKAVSGLLTHTTLLKALG | 17 |
| ML1-H2 | LQLHVLKAVSGLLTLTMIRRALG | 18 |
| ML1-H3 | LQLHVLKAVAGLRTLAMIRRALA | 19 |

TABLE 4

| Peptide Name | Number of Residues | Molecular Weight | Absorbance Coefficient | Isoelectric Point | Net Charge (pH 7) | Predicted Solubility |
|---|---|---|---|---|---|---|
| ML1 | 23 | 2461.9 g/mol | 0 $M^{-1}cm^{-1}$ | pH 11.23 | 2.1 | Low solubility in water |
| ML1-H1 | 23 | 2426.94 g/mol | 0 $M^{-1}cm^{-1}$ | pH 10.73 | 2.2 | Low solubility in water |
| ML1-H2 | 23 | 2504.09 g/mol | 0 $M^{-1}cm^{-1}$ | pH 12.13 | 3.1 | Low solubility in water |
| ML1-H3 | 23 | 2515.12 g/mol | 0 $M^{-1}cm^{-1}$ | pH 12.41 | 4.1 | Low solubility in water |

Example 3. Erythropoietin-Derived Peptides Using Partial Sequence (2)

Figure 8:
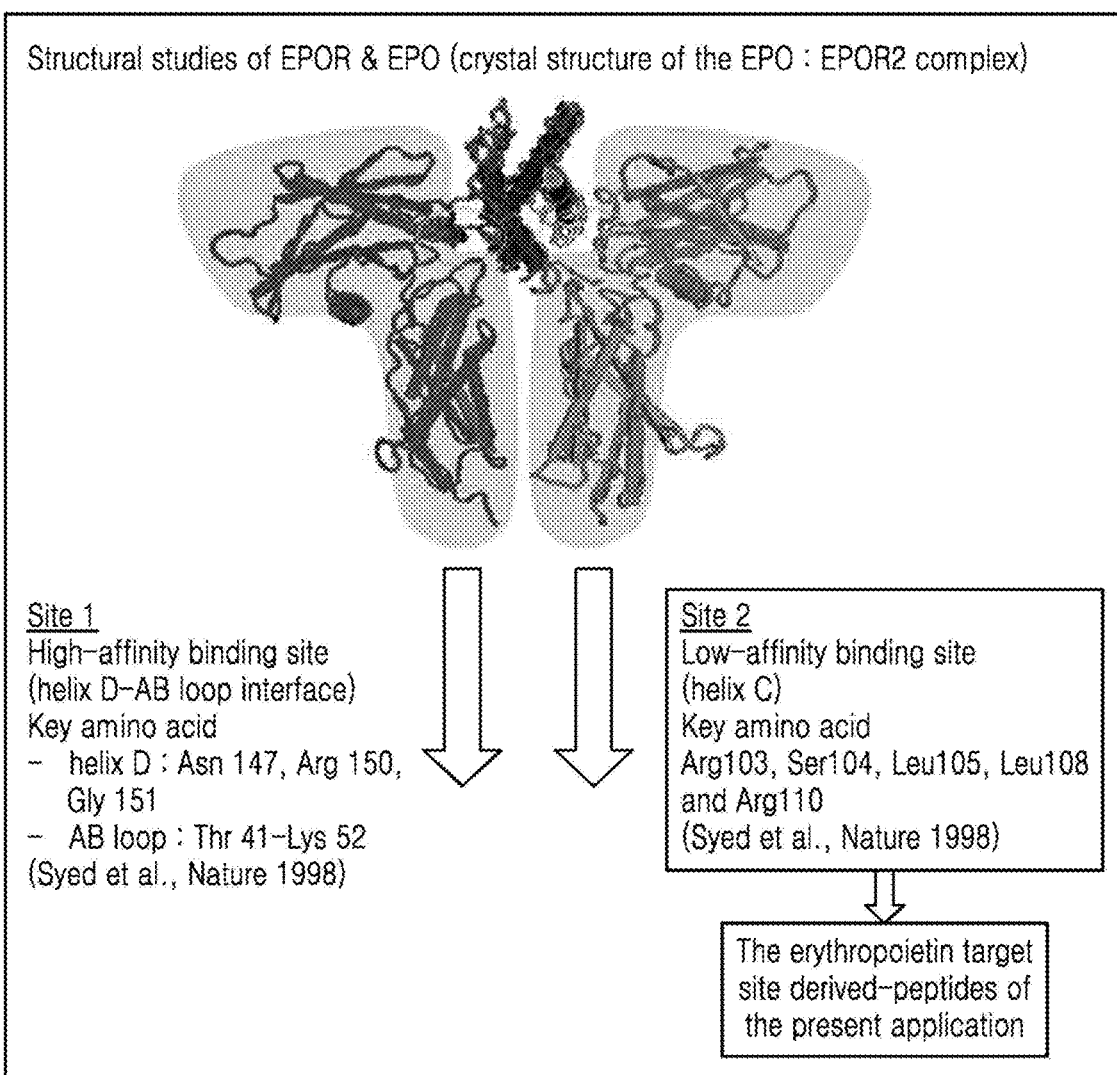
FIG. 8 shows an illustration of a structure of a complex of erythropoietin receptor (EPOR) and erythropoietin (EPO) of a specific embodiment and binding target sites.

Partial sequences of the peptides were substituted using the basic sequence of ML1 as in Example 2. In this regard, amino acids were substituted based on the existing binding model of erythropoietin and its receptor without hindering the existing binding structure (a distance between proteins or a protein structure). FIG. 8 illustrates exemplary substitution of amino acid sequences, and since substitution of alanine (Ala) with arginine (Arg) hinders the existing binding, substitution with serine (Ser) may be performed to prevent hindrance of the binding.

Peptides prepared by modifying the charge of the ML1 peptide and characteristics thereof are shown in Tables 5 and 6.

TABLE 5

| Peptide Name | Sequence | SEQ ID NO |
|---|---|---|
| ML1-C1 | LDLEVDKAVSGLRSLTTLLRALG | 20 |
| ML1 | LQLHVDKAVSGLRSLTTLLRALG | 1 |
| ML1-C2 | LQRHVDKRVSGLRSLTTLLRALG | 21 |
| ML1-C3 | LQRHVKKRVKGLKSLTTLLRALG | 22 |

TABLE 6

| Peptide Name | Number of Residues | Molecular Weight | Absorbance Coefficient | Isoelectric Point | Net Charge (pH 7) | Predicted Solubility |
|---|---|---|---|---|---|---|
| ML1-C1 | 23 | 2440.83 g/mol | 0 $M^{-1}cm^{-1}$ | pH 6.96 | 0 | High solubility in water |
| ML1 | 23 | 2461.9 g/mol | 0 $M^{-1}cm^{-1}$ | pH 11.23 | 2.1 | Low solubility in water |
| ML1-C2 | 23 | 2590.04 g/mol | 0 $M^{-1}cm^{-1}$ | pH 12.12 | 4.1 | High solubility in water |
| ML1-C3 | 23 | 2616.21 g/mol | 0 $M^{-1}cm^{-1}$ | pH 12.45 | 7.1 | High solubility in water |

Example 4. Erythropoietin-Derived Peptides Using Partial Sequence (3)

A partial sequence "LHVDKAVSGLRSLTTL" of the ML1 basic sequence was used to prepare peptides having modified amino acids at both ends thereof, as shown in Table 7 below.

TABLE 7

| Peptide Name | Sequence | SEQ ID NO |
|---|---|---|
| ML1-L2 | L HVDKAVSGLRSLTT L | 23 |
| ML1-K2 | K HVDKAVSGLRSLTT K | 24 |
| ML1-R2 | R HVDKAVSGLRSLTT R | 25 |

Example 5. Erythropoietin-Derived Peptides for Use In Vivo (4)

Using sequences of the ML1, ML1-C3, and ML1-H2, as shown in Table 8 below, peptides, each of which has two amino acids removed from both ends thereof, excluding key regions, to improve efficiency and stability, were additionally prepared.

Sequences of the additionally prepared MLP, MLP-C, and MLP-H peptides and characteristics thereof are shown in Tables 8 and 9.

TABLE 8

| Peptide Name | Sequence | SEQ ID NO |
|---|---|---|
| MLP | LHVDKAVSGLRSLTTLLRA | 26 |
| MLP-C | RHVKKRVKGLKSLTTLLRA | 27 |
| MLP-H | LHVLKAVSGLLTLTMIRRA | 28 |

TABLE 9

| Peptide Name | Number of Residues | Molecular Weight | Absorbance Coefficient | Isoelectric Point | Net Charge (pH 7) | Predicted Solubility |
|---|---|---|---|---|---|---|
| MLP | 19 | 2050.41 g/mol | 0 M$^{-1}$cm$^{-1}$ | pH 11.23 | 2.1 | High solubility in water |
| MLP-C | 19 | 2204.71 g/mol | 0 M$^{-1}$cm$^{-1}$ | pH 12.45 | 7.1 | High solubility in water |
| MLP-H | 19 | 2590.04 g/mol | 0 M$^{-1}$cm$^{-1}$ | pH 12.13 | 3.1 | Low solubility in water |

Experimental Example

Determination of Binding Affinity of Erythropoietin-Derived Peptide to Erythropoietin Receptor (EPOR)

To determine whether the erythropoietin-derived peptides prepared in Examples 1 to 3 are able to bind to the erythropoietin receptor having the target site to exert their actions, a surface plasmon resonance (SPR) technique was used to determine binding affinity. The SPR technique is to measure interactions between biomolecules in real-time by using an optical principle without specific labeling, and is a system analyzing affinity between two molecules and kinetics, i.e., an association rate (Ka) and a dissociation rate (Kd).

In detail, real-time SPR analysis was performed using Reichert SPR Biosensor SR 7500C instrument (Reichert Inc., NY, USA). Soluble mouse EPOR chimera proteins (R&D Systems, Minneapolis, MN, USA) were covalently linked to a carboxymethylated dextran matrix-coated chip (BR-1005-39, Pharmacia Biosensor AB) by an amine coupling procedure using an amine coupling kit (BR-1000-50, GE Healthcare, USA) in accordance with manufacturer's instructions. Each 5 µM, 2.5 µM, and 1.25 µM of the peptide samples of the present disclosure and scrambled peptides were applied at a flow rate of 5 µl/minute, and the experiments were independently performed in duplicate. For signal normalization, DMSO was applied at a flow rate of 5 µl/minute, and after each binding cycle, the sensor chip was regenerated by injecting 25 mM acetic acid at a flow rate of 20 µl/minute.

Figure 2A:
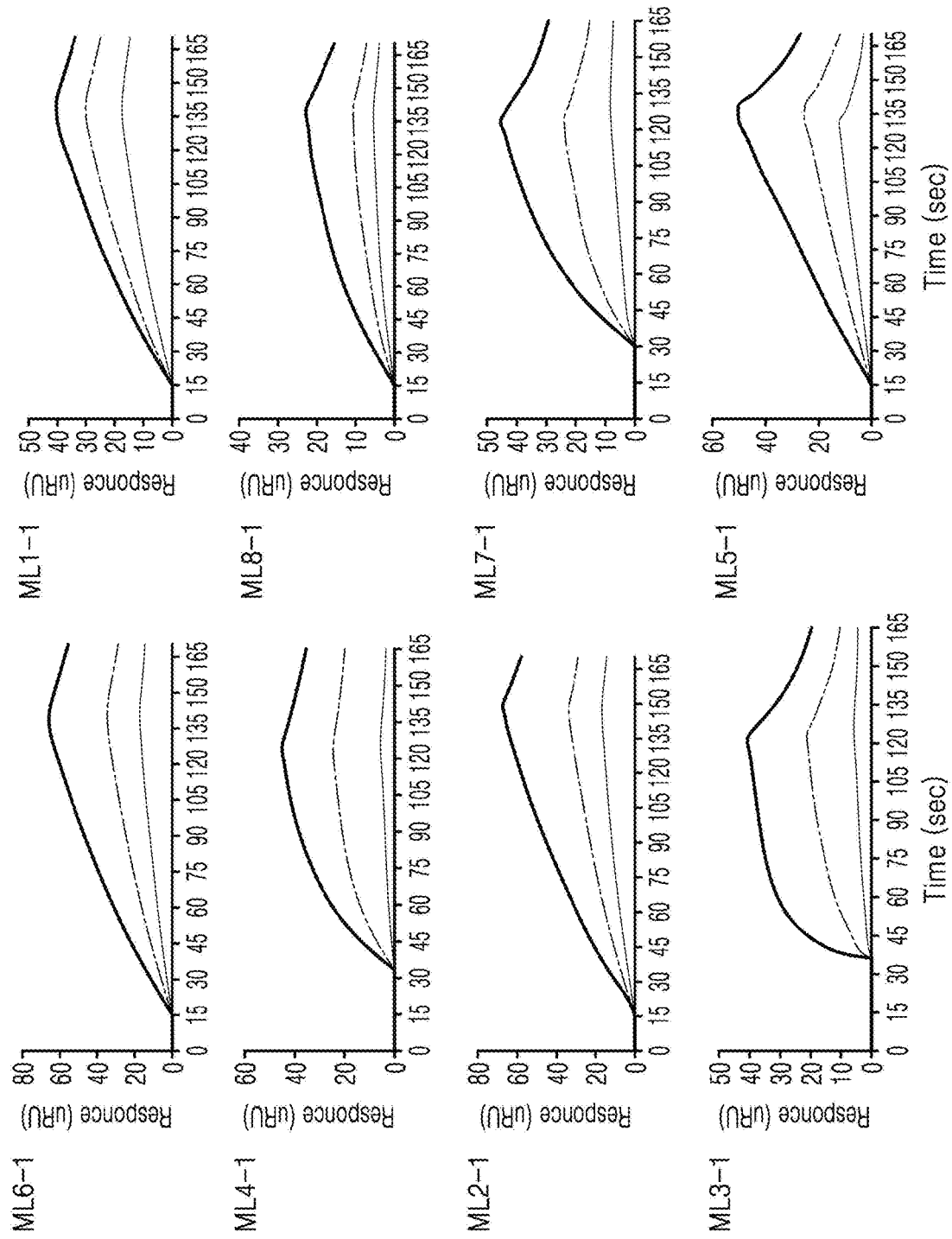
Figure 2B:
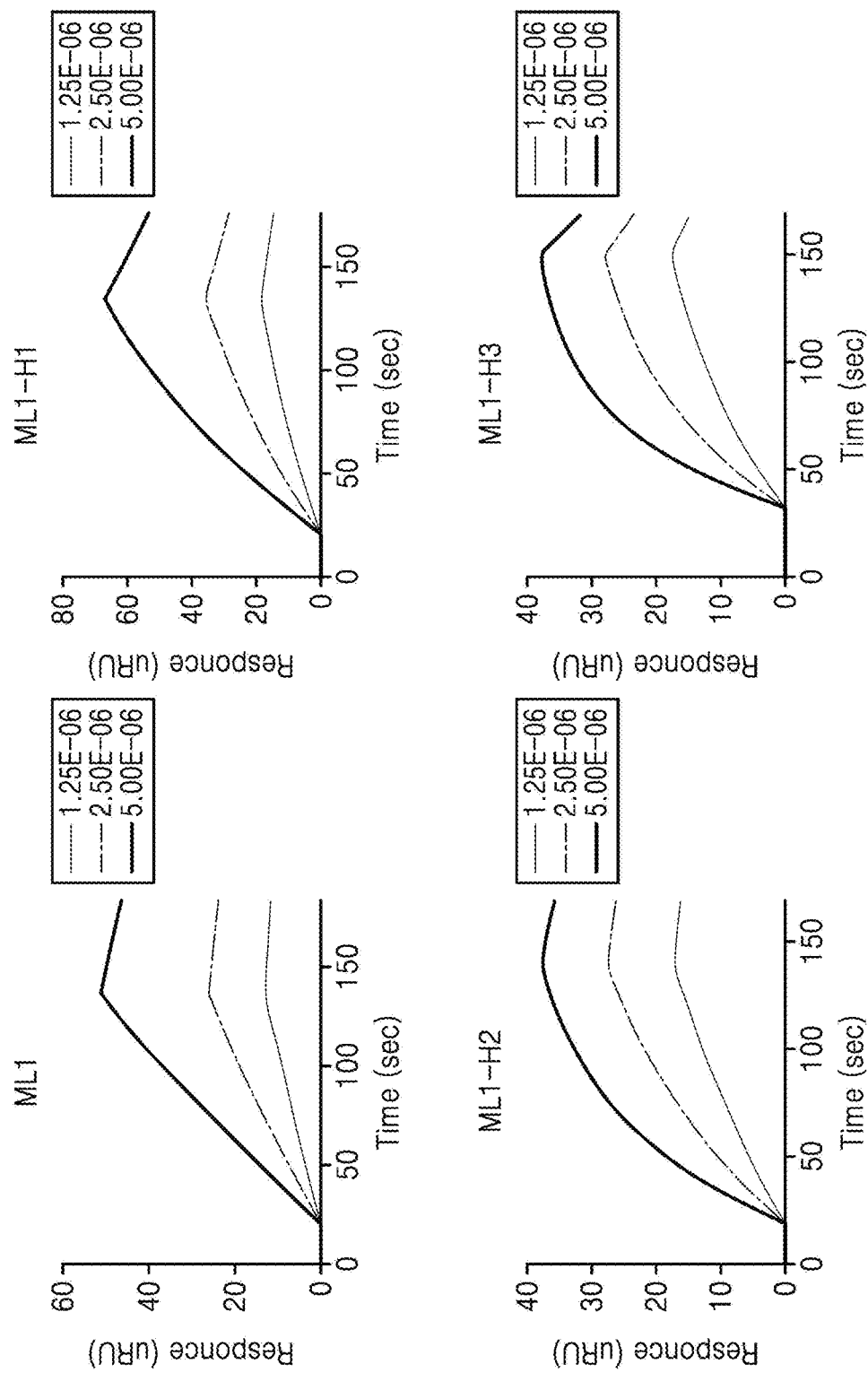
Figure 3A:
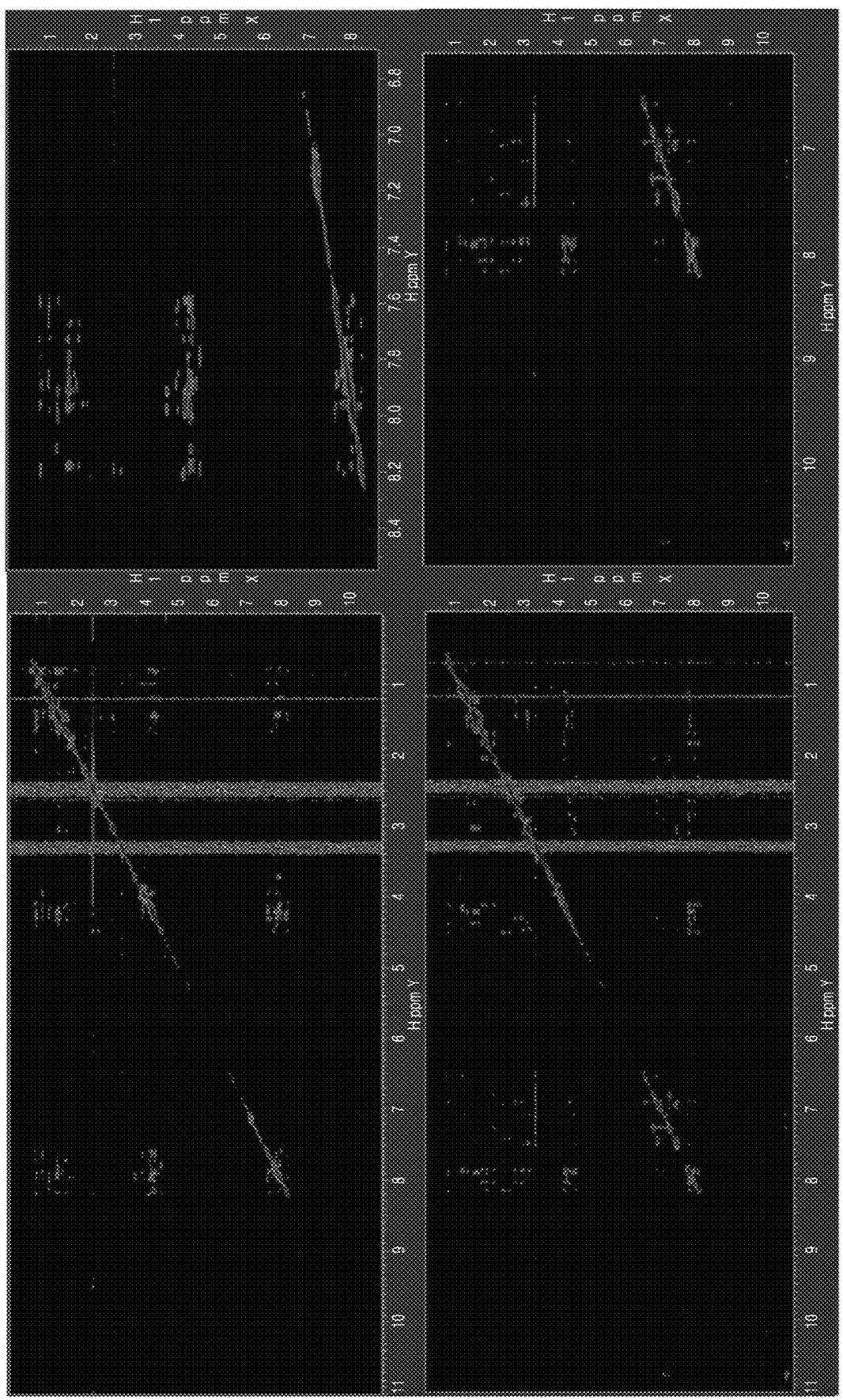
FIG. 3A-3D are photographs confirming a secondary alpha helix formation of an erythropoietin-derived peptide (ML1, ML1-C1, ML1-C2, ML1-C3, ML1-H1, ML1-H2, and ML1-H3).
Figure 3B:
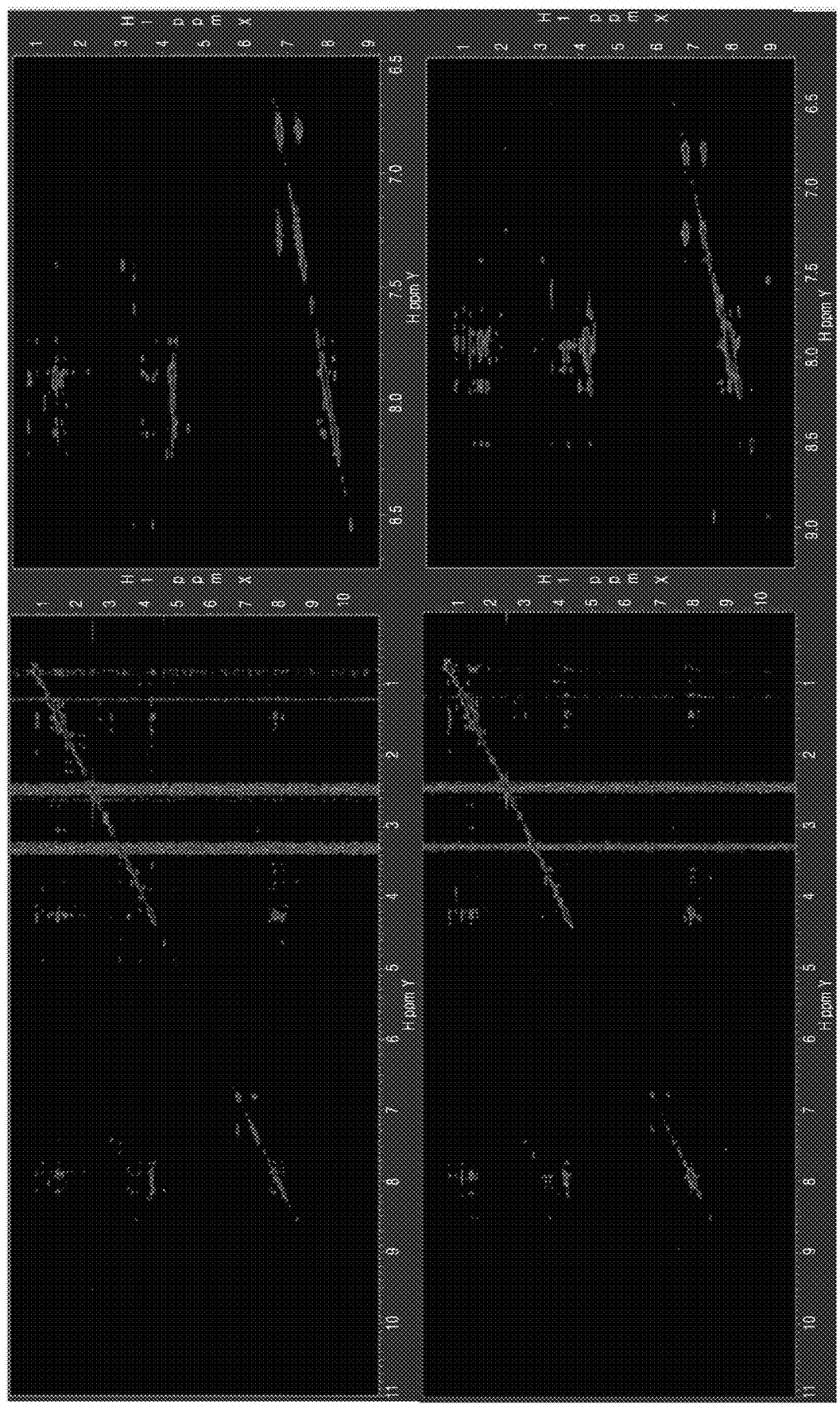
Figure 3C:
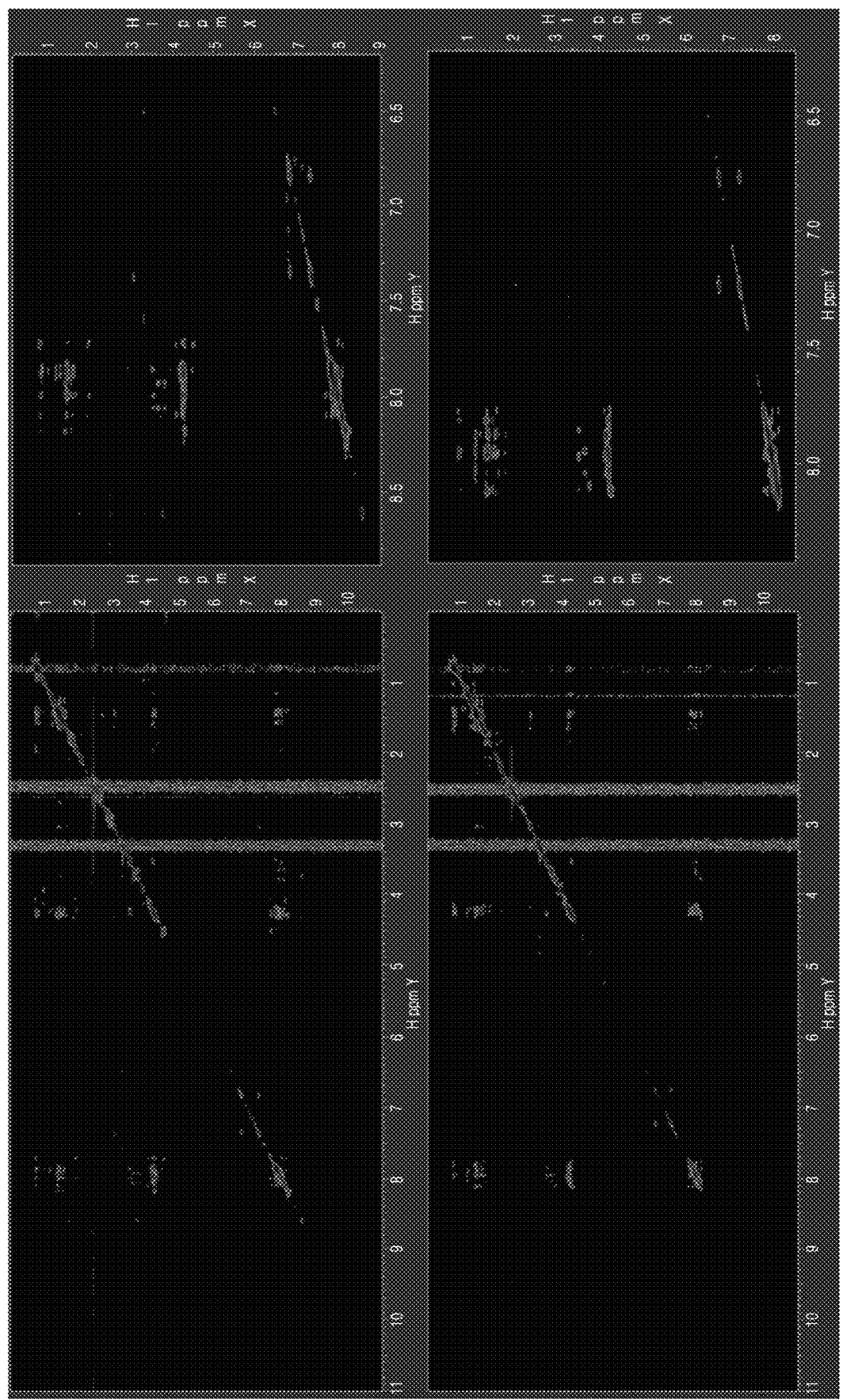
Figure 3D:
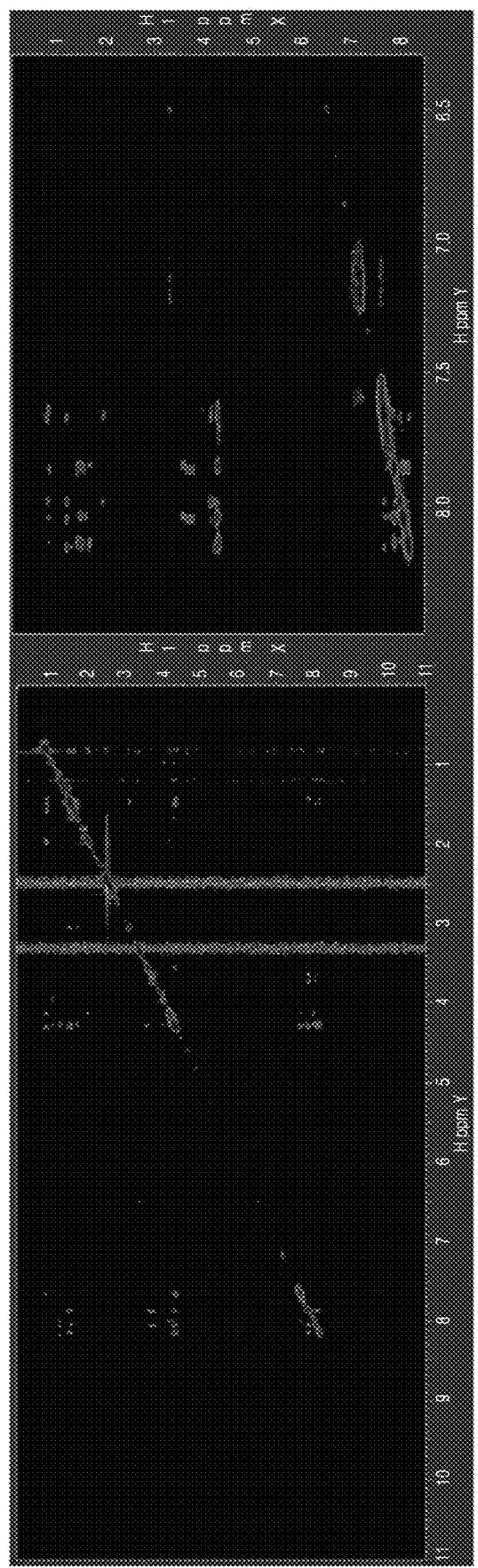
Figure 4A:
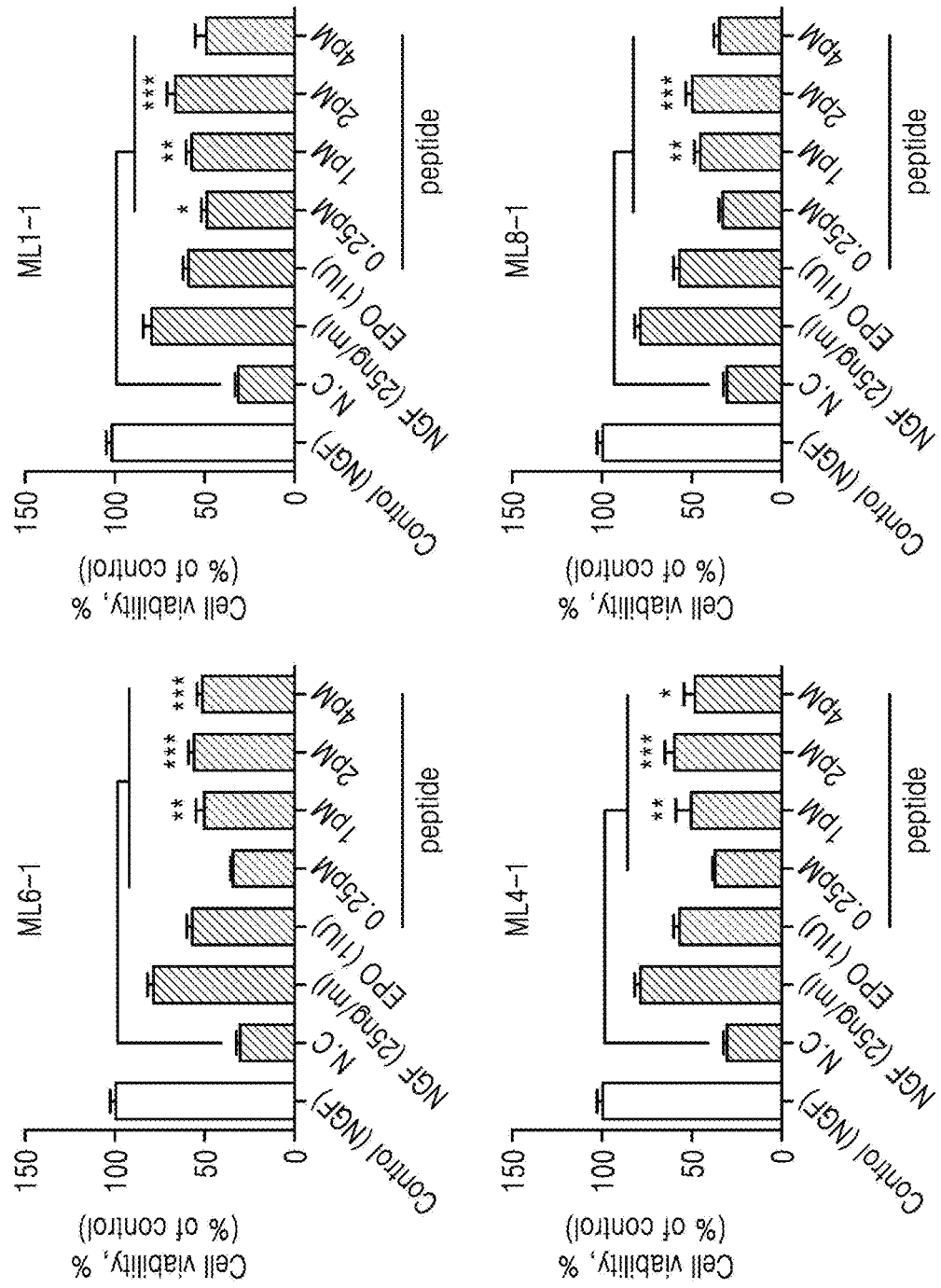
FIGS. 4A-4D depict graphs showing cell protective effects of erythropoietin-derived peptide treatment of cells in which reactive oxygen species were increased by hydrogen peroxide.
Figure 4B:
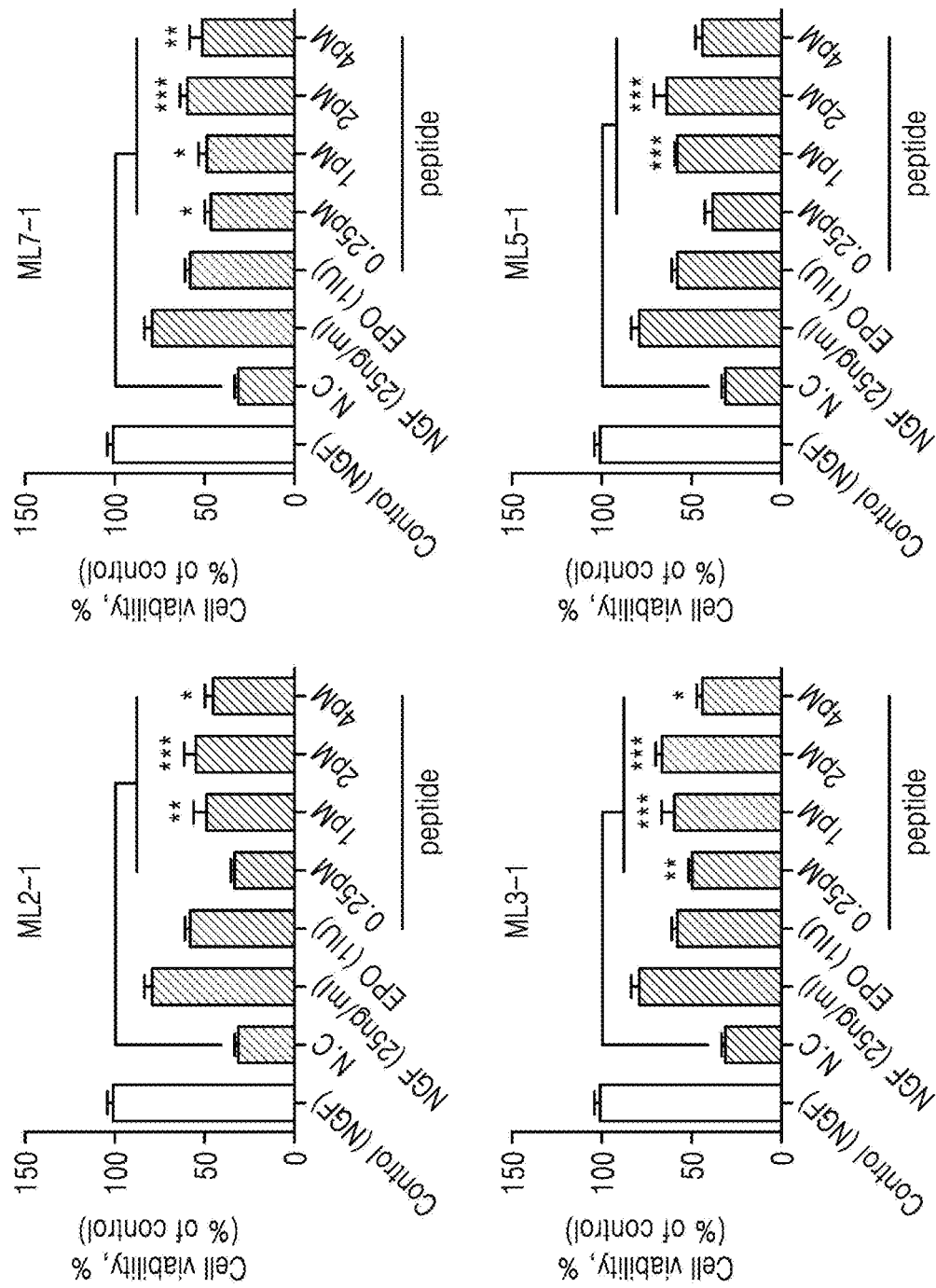
Figure 4C:
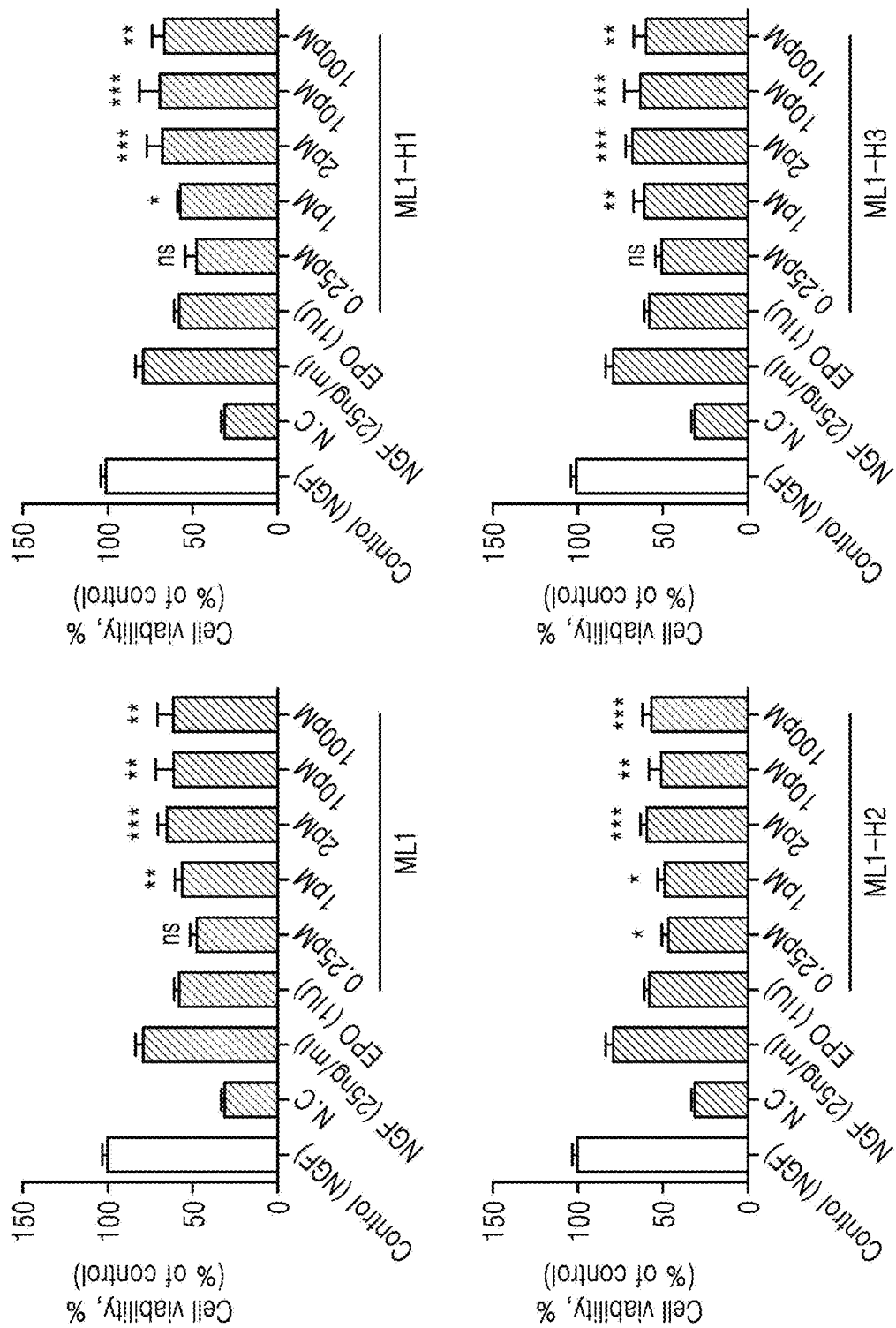
Figure 4D:
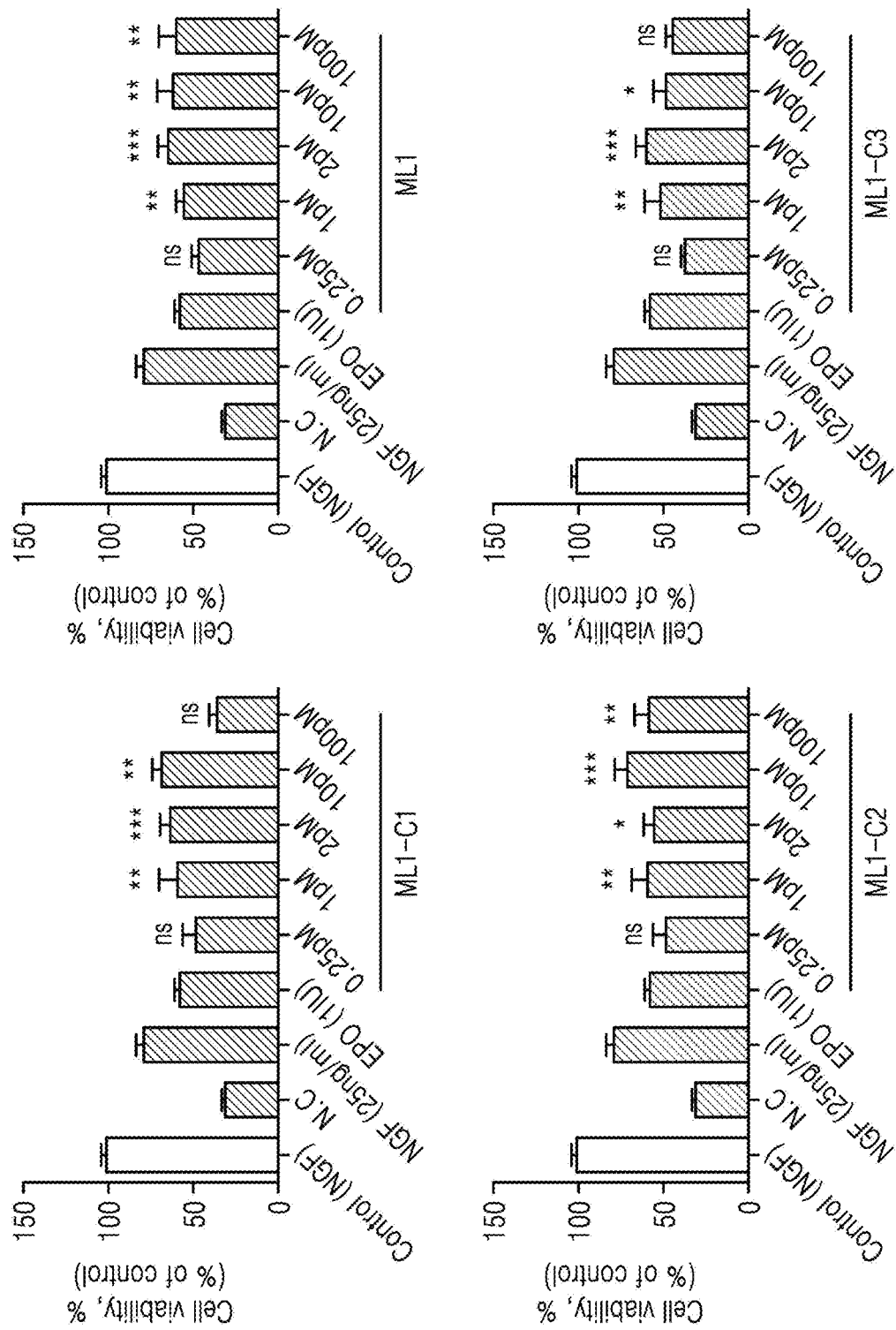

As a result, as shown in FIG. 2, the result values were increased according to the concentrations of the erythropoietin-derived peptides of one embodiment, and thus, it was confirmed that the erythropoietin-derived peptides were able to bind to the erythropoietin receptor having the target site to exert their actions. Further, as shown in Tables 10 and 11, it was also confirmed that the erythropoietin-derived peptides of specific embodiments exhibited binding affinities similar to the known binding affinity (~1 uM).

TABLE 10

| | Ka | Kd | KD |
|---|---|---|---|
| ML1 | 1.311 × 10$^3$ | 8.5 × 10$^{-3}$ | 6.46077 µM |
| ML2 | 1.6 × 10 | 4.4 × 10$^{-3}$ | 273 µM |
| ML3 | 2.05 × 10$^2$ | 3 × 10$^{-3}$ | 14.6341 µM |
| ML4 | 2.2 × 10$^2$ | 2.2 × 10$^{-3}$ | 10 µM |
| ML5 | 3.04 × 10$^2$ | 0.1 × 10$^{-3}$ | 0.32894 µM |
| ML6 | 5.0 × 10 | 4.5 × 10$^{-2}$ | 900 µM |
| ML7 | 3.00 × 10$^2$ | 0.2 × 10$^{-2}$ | 6.666 µM |
| ML8 | 1.8 × 10$^2$ | 0.8 × 10$^{-1}$ | 444.44 µM |
| ML1-1 | 5.55 × 10$^3$ | 5.9 × 10$^{-3}$ | 1.06 µM |
| ML2-1 | 3.1 × 10$^2$ | 4.1 × 10$^{-3}$ | 14.3 µM |
| ML3-1 | 3.08 × 10$^3$ | 1.3 × 10$^{-2}$ | 4.31 µM |
| ML4-1 | 4.10 × 10$^2$ | 1.20 × 10$^2$ | 39.34 mM |
| ML5-1 | 4.42 × 10$^2$ | 3.46 × 10$^{-2}$ | 78.28 µM |
| ML6-1 | 1.9 × 10$^2$ | 3 × 10$^{-2}$ | 157.8 µM |
| ML7-1 | 2.26 × 10$^2$ | 1.44 × 10$^{-2}$ | 63.70 µM |
| ML8-1 | 6.4 × 10 | 1.5 × 10$^{-1}$ | 2.37 mM |

TABLE 11

| | Km | Ka | Kd | KD |
|---|---|---|---|---|
| ML1 | 1.26E+05 | 1310.8 | 8.47E−03 | 6.46077 µM |
| ML1-H1 | 4.79E+05 | 1.01E+03 | 7.94E−03 | 7.84542 µM |
| ML1-H2 | 1.00E+10 | 3434.3 | 1.05E−03 | 306.977 nM |
| ML1-H3 | 1.00E+10 | 4157.6 | 4.77E−03 | 1.14651 µM |
| ML1-C1 | 9.23E+05 | 1745.7 | 0.2617 | 149.921 µM |
| ML1-C2 | 4.58E+05 | 1.59E+03 | 0.01876 | 11.7609 µM |
| ML1-C3 | 1.46E+05 | 1104.9 | 0.01086 | 9.82836 µM |

In other words, it could be confirmed that the peptides according to specific embodiments are those derived from the erythropoietin binding site, and thus have binding affinity to the erythropoietin receptor.

Determination of Secondary Alpha-Helix Formation of Erythropoietin-Derived Peptide It was determined whether the erythropoietin-derived peptides synthesized in Examples 2 and 3 are able to form a stable alpha-helix, like natural erythropoietin.

As a result, as shown in FIG. 3A-3D, it was confirmed that the erythropoietin-derived peptides synthesized in Examples 2 and 3 formed a stable secondary alpha-helix, like natural erythropoietin.

Determination of Cell Protective Effect of Erythropoietin-Derived Peptide (1)

To determine whether the erythropoietin-derived peptides prepared in Examples 1 to 3 exhibit cell protective effects, cell viability was determined under stress conditions where an increase in reactive oxygen species was induced by hydrogen peroxide (H$_2$O$_2$).

In detail, to evaluate cell viability, an MTS assay (Cell-Titer 96 Aqueous One Solution Cell Proliferation Assay, Promega, Madison, Wis., USA) was performed. PC12 cells were seeded in a 96-well plate (5×10$^4$ cells per well), and an increase in reactive oxygen species was induced using 150 µM of hydrogen peroxide (H$_2$O$_2$). Thereafter, 25 ng/ml of nerve growth factor (NGF) was added as a positive control group, and 1 IU/ml of the erythropoietin compound, 0.25 pM, 1 pM, 2 pM, or 4 pM of the peptide of Example 1, each 0.25 pM, 1 pM, 2 pM, 10 pM, or 100 pM of the peptides of Examples 2 and 3, or 0.1 pM, 1 pM, 50 pM, or 0.5 nM of the peptide of Example 4 was added, and 20 µl of an MTS solution was added to each well, and left for 3 hours. The initial number of cells (0 hour) and the number of cells after 48 hours were counted. Intracellular soluble formazan produced by cell reduction was determined by recording absorbance of each 96-well plate at a wavelength of 490 nm using a VERSA MAX.

As a result, as shown in FIG. 4, it was confirmed that the erythropoietin-derived peptides protected cells from cell death caused by the increase in reactive oxygen species. It could be confirmed that this result was similar to the cell protective effect by treatment with the natural erythropoietin compound.

Determination of Cell Protective Effect of Erythropoietin-Derived Peptide (2)

To determine whether the erythropoietin-derived peptide prepared in Example 4 exhibits the cell protective effect, mitochondrial activity was determined under stress conditions where an increase in reactive oxygen species was induced by hydrogen peroxide ($H_2O_2$).

In detail, PC12 cells or human SH-SY5Y cells were seeded in a 96-well plate ($5 \times 10^4$ cells per well), and an increase in reactive oxygen species was induced using 150 µM of hydrogen peroxide ($H_2O_2$). Thereafter, 25 ng/ml of NGF was added as a positive control group, and 1 IU/ml of the erythropoietin compound, or 0.1 pM, 1 pM, 50 pM, or 0.5 nM of the peptide of Example 4 was added.

When mitochondrial activity is suppressed, mitochondrial swelling due to abnormalities of the mitochondrial membrane potential, dysfunction due to oxidative stress such as reactive oxygen species or free radicals, dysfunction due to genetic factors, and dysfunction due to defects in oxidative phosphorylation for mitochondrial energy production occur. Thus, mitochondrial activity may be determined by measuring the mitochondrial membrane potential. Tetramethylrhodamine methyl ester (TMRM) staining of mitochondria was performed, and since TMRM staining intensity is increased in proportion to the mitochondrial membrane potential, the intracellular mitochondrial membrane potential was determined by measuring the TMRM staining intensity using a microplate reader (excitation, 485 nm; emission, 535 nm).

Figure 5A:
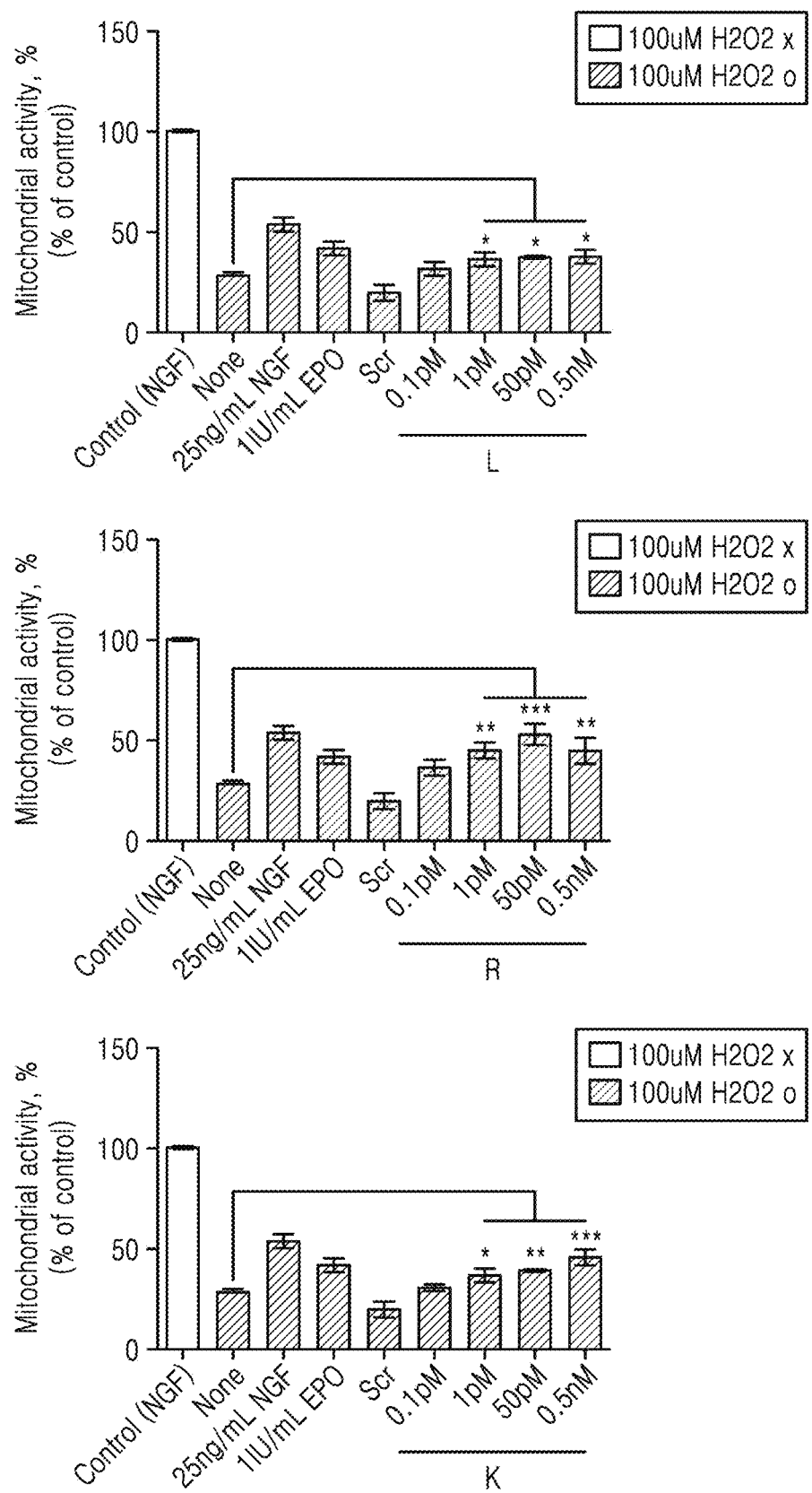
FIG. 5A-5B depict graphs showing cell protective effects of a peptide (ML1-L2, ML1-K2, and ML1-R2) prepared by partially modifying sequences of an erythropoietin-derived ML1 peptide.
Figure 5B:
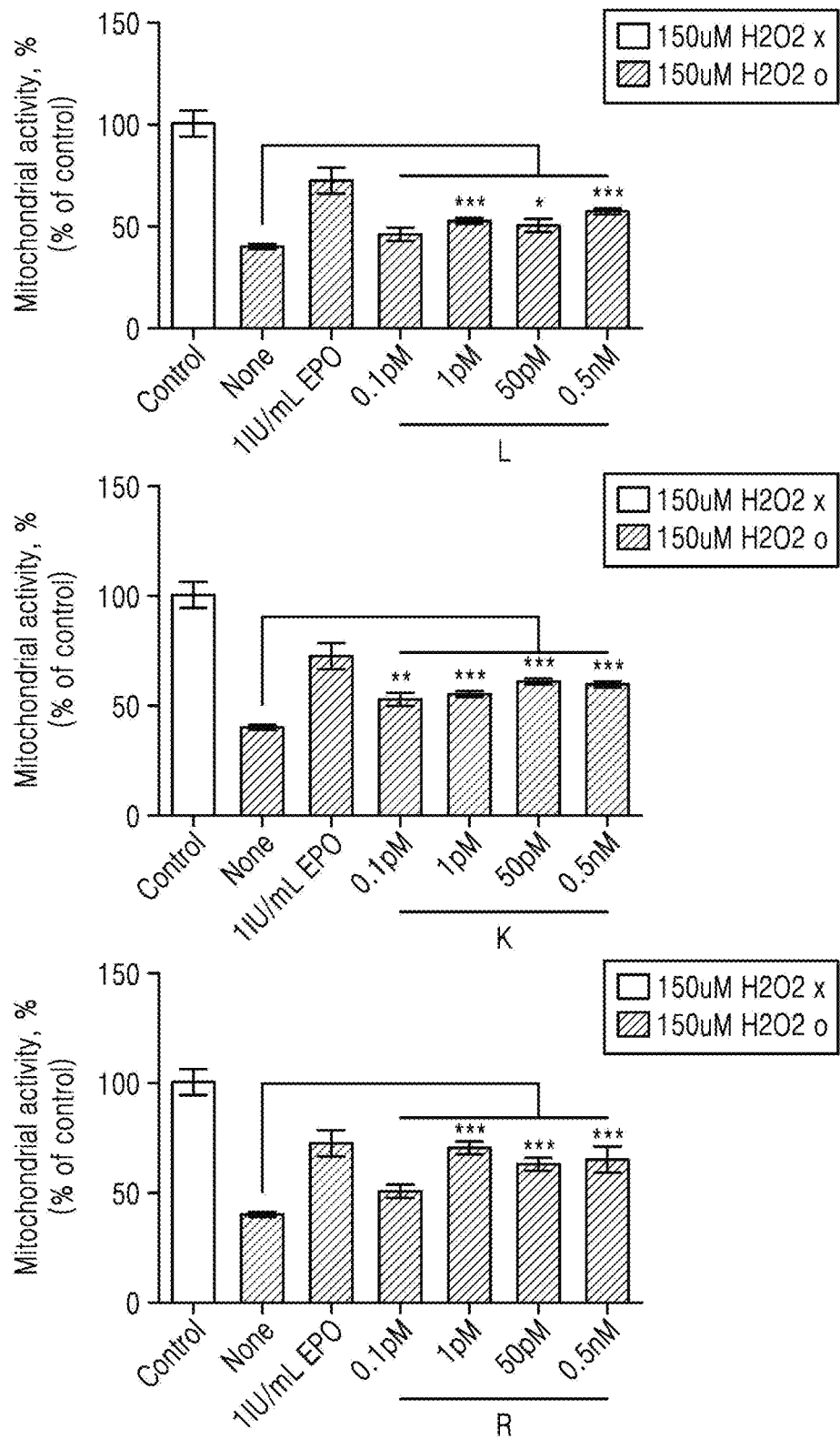

As a result, as shown in FIG. 5A-5B, it was confirmed that the erythropoietin-derived peptides suppressed inhibition of mitochondrial activity caused by increased reactive oxygen species. It could be confirmed that this result was similar to the effect by treatment with the natural erythropoietin compound.

Determination of Cell Proliferation-Inhibitory Effect of Erythropoietin-Derived Peptide Side effects such as cell proliferation were determined for the three peptides (ML1-L2, ML1-K2, and ML1-R2) prepared in Example 4.

In detail, to determine cell proliferation degree, an MTS assay (CellTiter 96 Aqueous One Solution Cell Proliferation Assay, Promega, Madison, Wis., USA) was performed. PC12 cells were seeded in a 96-well plate ($5 \times 10^4$ cells per well), and 1 pM of scrambled peptide (Scr) as a negative control group, 0.5 IU/ml, 1 IU/ml, or 10 IU/ml of the erythropoietin compound, or 1 pM, 10 pM, or 0.5 nM of the peptide of Example 4 was added, and 20 µl of an MTS solution was added to each well, and left for 3 hours. The initial number of cells (0 hour) and the number of cells after 48 hours were counted. Intracellular soluble formazan produced by cell reduction was determined by recording absorbance of each 96-well plate at a wavelength of 490 nm using a VERSA MAX.

Figure 6:
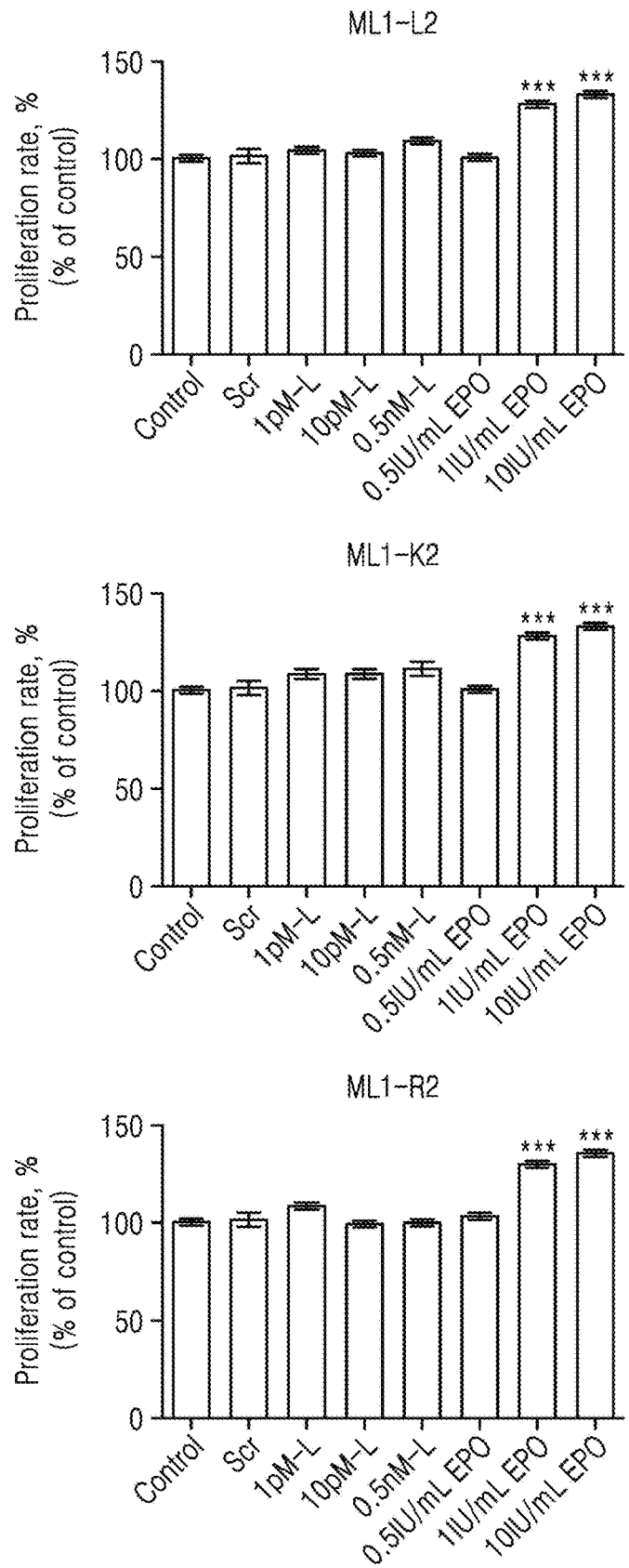
FIG. 6 depicts graphs showing cell proliferation rates of a peptide (ML1-L2, ML1-K2, and ML1-R2) prepared by partially modifying sequences of an erythropoietin-derived ML1 peptide.

As a result, as shown in FIG. 6, it was confirmed that all the peptides showed cell proliferation rates similar to that of the control group, and showed no side effect of cell proliferation.

Determination of Cell Proliferation-Inhibitory and -Enhancing Effects of Erythropoietin-Derived Peptide To determine the side effect, such as cell proliferation, of the peptides prepared in Examples 1 to 3, cell viability was evaluated by an MTT assay.

In detail, PC12 cells were cultured in a DMEM (Dulbecco's Modified Eagle's Medium) medium (Hyclone, USA) and an RPM11640 medium (Hyclone, UT, USA), each supplemented with 10% fetal bovine serum (FBS, Hyclone, Utah, USA), 100 unit/ml penicillin, and 100 µg/ml streptomycin (Hyclone, UT, USA) in an incubator supplied with 5% $CO_2$ and under a condition of 37° C. PC12 cell lines were seeded in a 96-well plate at a density of $5 \times 10^4$ cells/ml, and cultured under conditions of 37° C. and 5% $CO_2$ for 24 hours. Thereafter, the cells were treated with each of the peptides of Examples 1 to 3, which were prepared at a concentration of 10 ng/ml, followed by incubation for 24 hours. Thereafter, 20 µl of 5 mg/ml 3-[4,5-dimethyl-thiazol]-2,5-diphenyl-tetrazolium bromide (MTT) reagent was added thereto, and allowed to react for 2 hours. After reaction, 200 µl of dimethyl sulfoxide (DMSO, Duksan, Gyeonggi-do, Korea) was added thereto to completely dissolve formed formazan, and absorbance at 570 nm was measured using a microplate reader (Molecular Devices, CA, USA).

Figure 7:
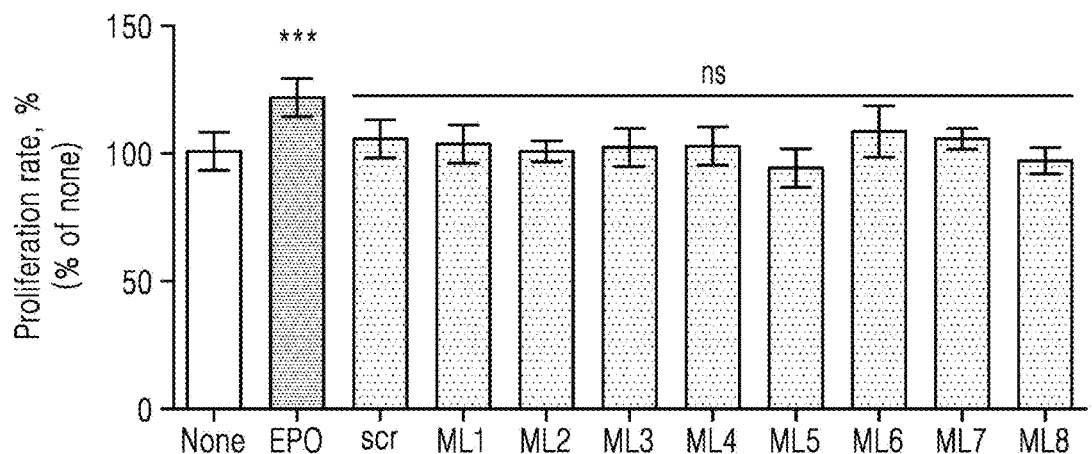
FIG. 7 depicts graphs showing cell proliferation rates of an erythropoietin-derive peptide and peptides prepared by partially modifying sequences.
Figure 7:
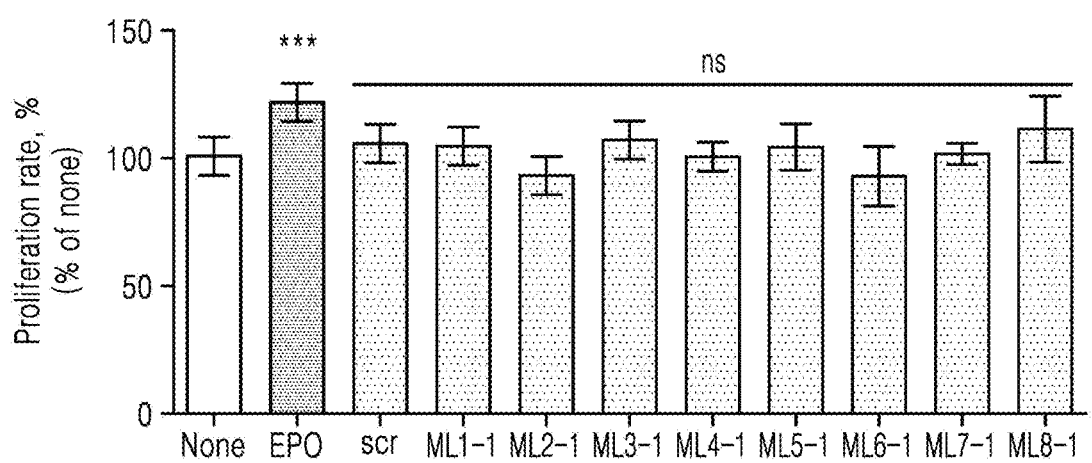
Figure 7:
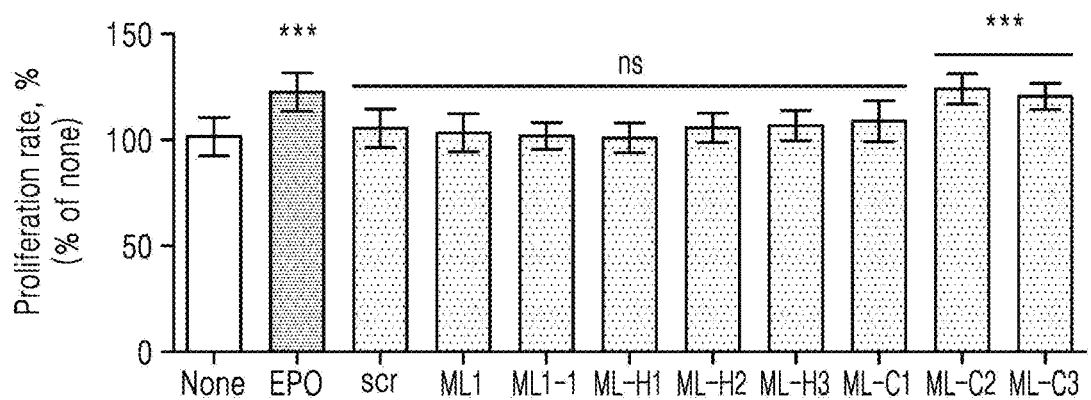

As a result, as shown in FIG. 7, it was confirmed that all the peptides showed cell proliferation rates similar to that of the control group, while ML1-C2 and ML1-C3 had cell proliferative effects to a degree similar to that of the natural erythropoietin. In other words, the peptides have cell proliferative effects similar to that of the natural erythropoietin and thus may be utilized as an alternative material therefor.

Comparison of Cell Protective and Proliferative Effects of Erythropoietin-Derived Peptide Cell protective and proliferative effects of the seven peptides (ML1, ML1-C1, ML1-C2, ML1-C3, ML1-H1, ML1-H2, and ML1-H3) prepared in Example 3 were statistically compared to that of EPO.

In detail, the effects shown in FIG. 4 and FIG. 7 were adjusted with respect to the effects by EPO and quantified, and clustering was performed by a K-means clustering algorithm.

Figure 9:
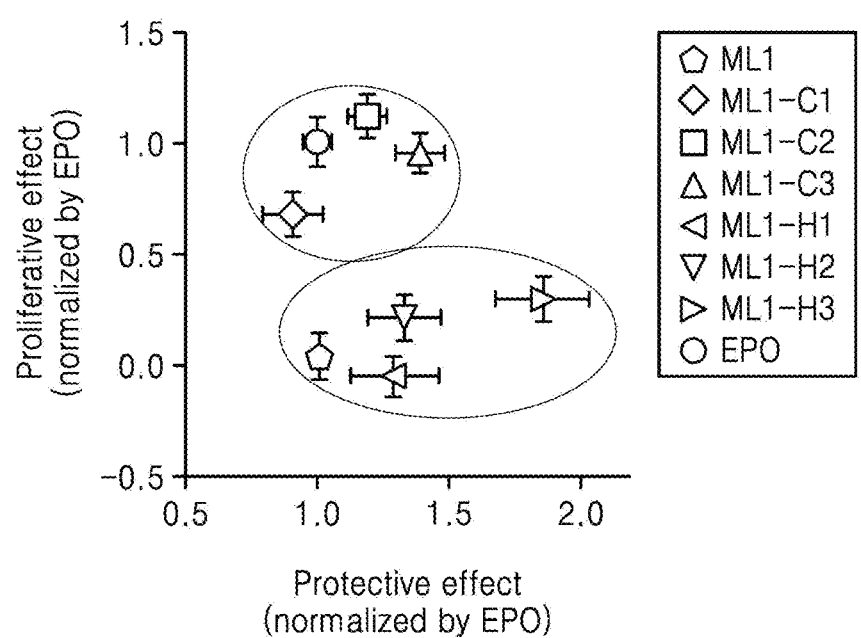
FIG. 9 depicts a graph showing cell protective and proliferative effects of an erythropoietin-derive peptide and peptides prepared by partially modifying sequences.

As a result, as shown in FIG. 9, ML1-C1, ML1-C2 and ML1-C3 were clustered as having similar effects as EPO in terms of cell protection and effects. However, it was analyzed that ML1, ML1-H1, ML1-H2, and ML1-H3 showed a large difference in terms of cell proliferative effects compared to EPO groups, while showing no large difference thereto in terms of cell protective effects.

Determination of In Vivo Hematopoietic Effects of Erythropoietin-Derived Peptide In vivo hematopoietic activities in a mouse were measured for the peptides prepared in Example 5, MLP, MLP-C, and MLP-H.

In detail, the prepared peptide or scrambled (Scr) peptide as a negative control group was administered by intraperitoneal injection to mice at a dose of 0 µg/kg, 1 µg/kg, or 100 µg/kg repeatedly, everyday over 14 days. Thereafter, a body weight test and a blood test were performed.

Figure 10:
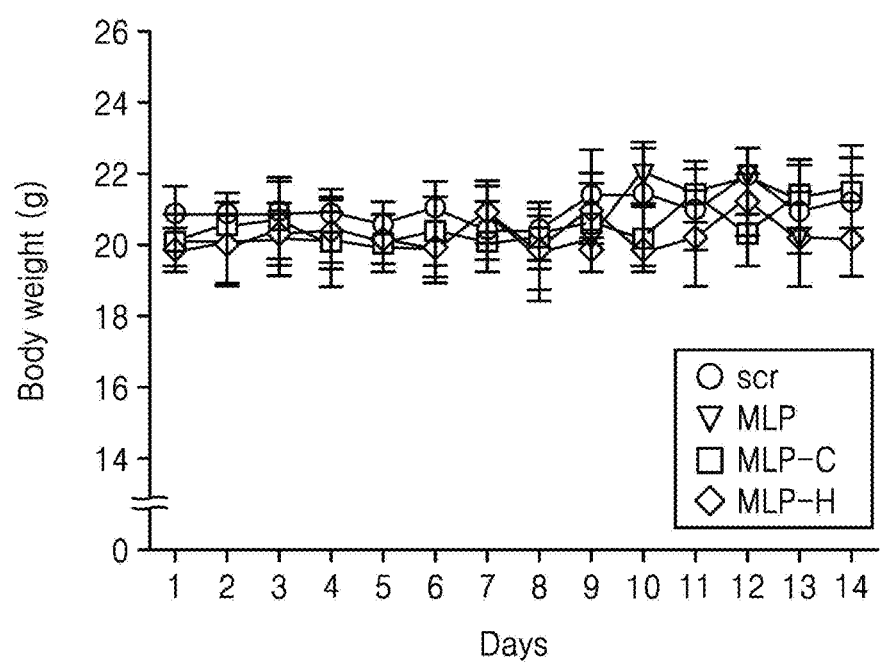
FIG. 10 depicts a graph showing effects of in vivo administration of an erythropoietin-derived peptide (MLP, MLP-C, and MLP-H) on body weight.
Figure 11A:
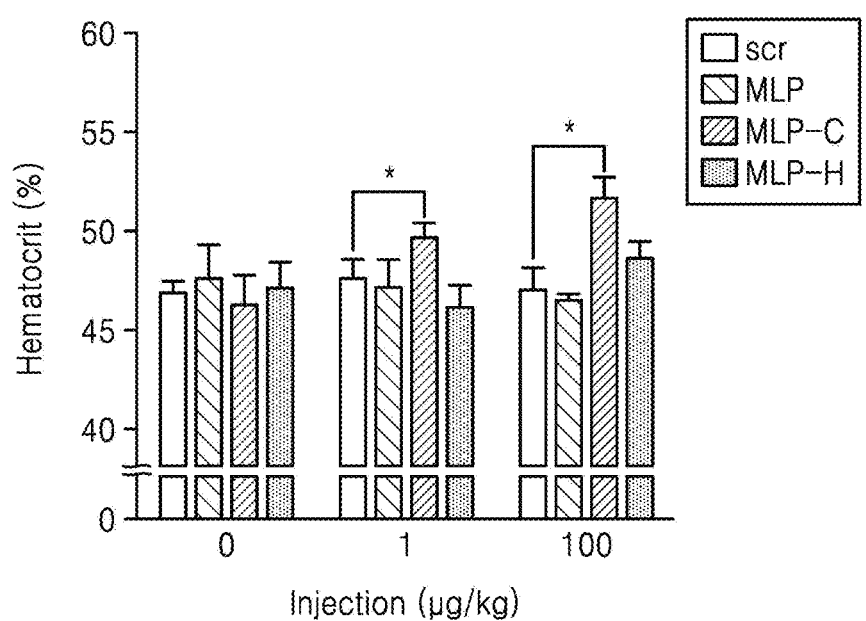
FIGS. 11A-11D depict graphs showing hematopoietic effects of in vivo administration of an erythropoietin-derived peptide (MLP, MLP-C, and MLP-H).
Figure 11B:
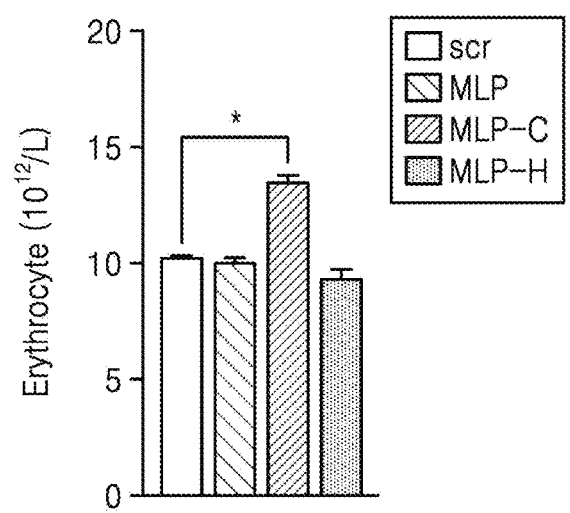
Figure 11C:
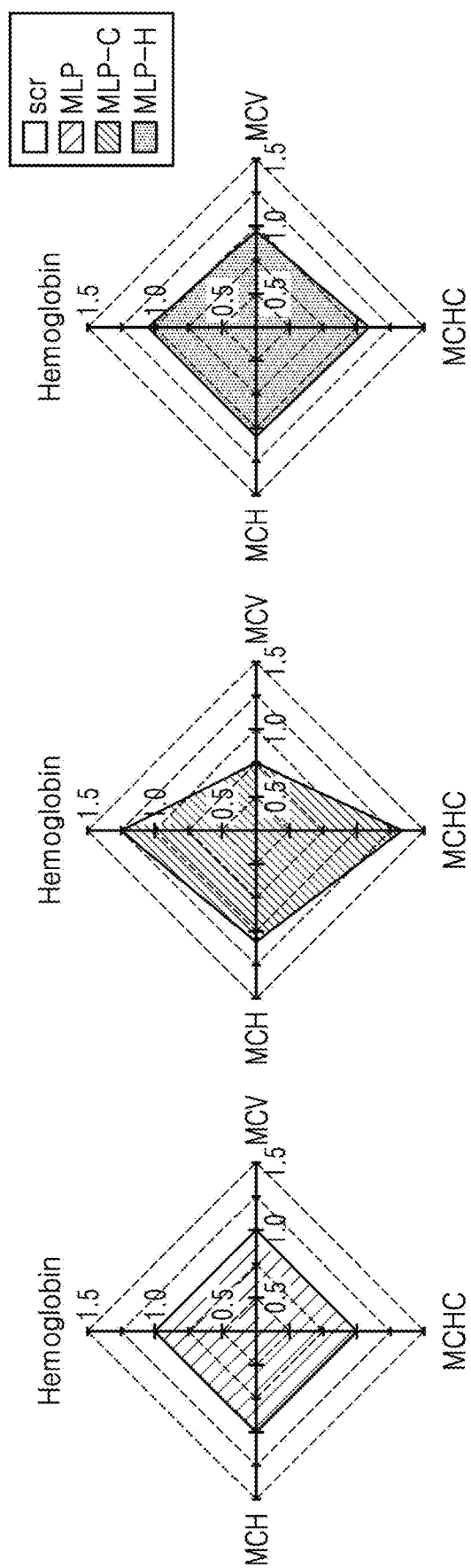
Figure 11D:
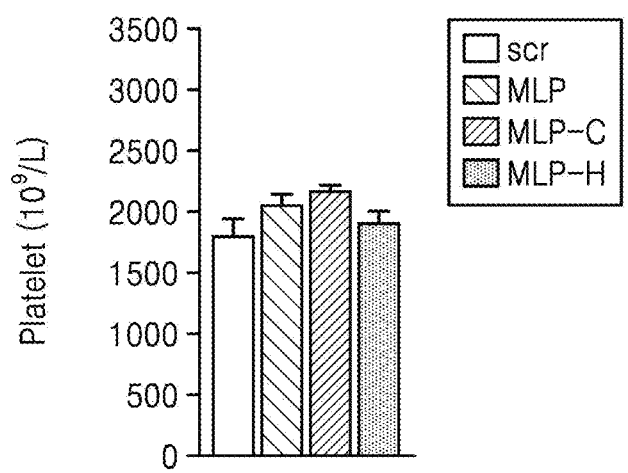

As a result, as shown in FIG. 10, it could be confirmed that all the peptides gave rise to no significant changes in body weight of the mice. Further, it could be confirmed that as shown in FIG. 11A, hematocrit, which is the volume of red blood cells in the blood expressed as a volume percentage, was significantly increased according to an administration dose only in the mice treated with MLP-C, and as shown in FIG. 11B, in case of the mice administered with 100 µg/kg, there were significant increases in red blood cell count, hemoglobin content, mean corpuscular hemoglobin concentration, and mean corpuscular hemoglobin. However, as shown in FIG. 11D, it could be confirmed that there was no large change in terms of platelet concentration. In other words, the peptide according to an aspect was able to induce hematopoiesis in vivo, and thus, the peptide is not only able to improve the hematopoietic function, but also may be used in the prevention or treatment of a hematopoietic disorder.

Determination of Erythropoietin Receptor (EPOR) Activation Regulation by Erythropoietin-Derived Peptide Erythropoietin receptor activation levels by MLP-C and MLP-H, among the peptides prepared in Example 5, were compared to that of the natural erythropoietin.

In detail, a DNA plasmid capable of expressing an erythropoietin receptor fused to green fluorescence protein was transfected into HEK 293 cell lines, and stable cell lines stably expressing the erythropoietin receptor fused to green fluorescence protein were prepared. After treatment with EPO as a positive control group, and MLP-C or MLP-H, a western blot was performed by sampling at time 0, 30, 60, and 90 minutes, and activation levels of the erythropoietin receptor were determined through ERK1/2 phosphorylation levels.

Figure 12A:
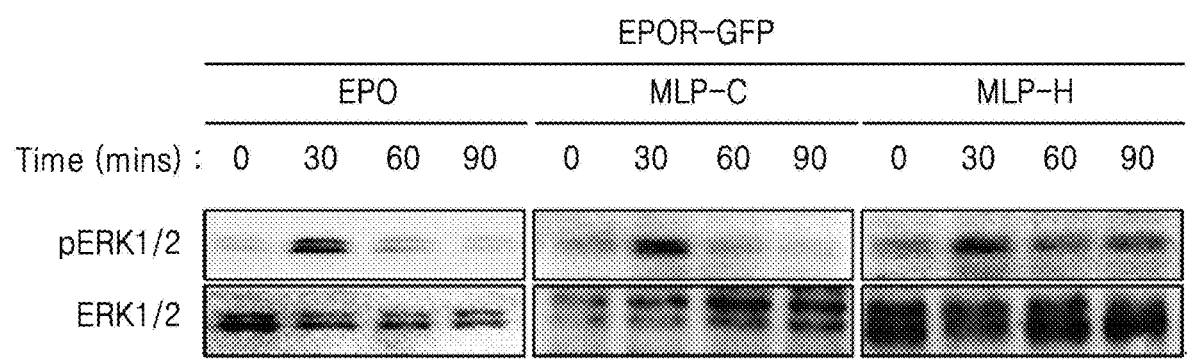
FIGS. 12A-12B show results of confirming activation regulating effects of an erythropoietin-derived peptide (MLP-C and MLP-H) and erythropoietin (EPO) with respect to an erythropoietin receptor.
Figure 12B:
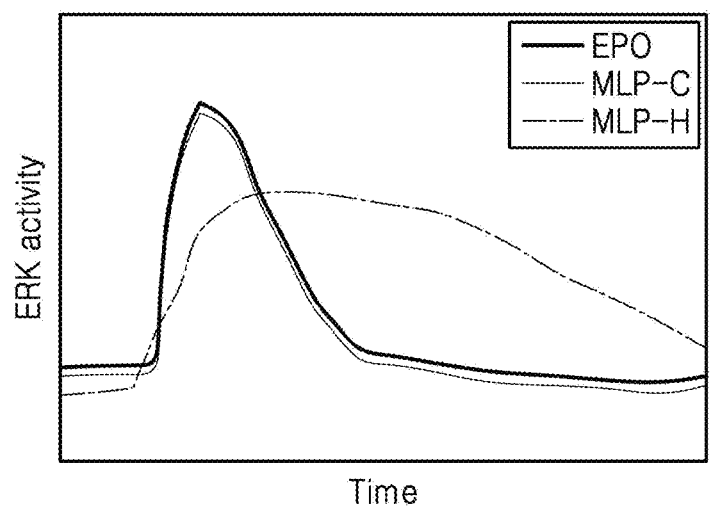

As a result, as shown in FIG. 12, it could be confirmed that, while EPO and MLP-C exhibit maximum activity at 30 minutes and decline thereafter, MLP-H maintains activation even after 30 minutes. In other words, while MLP-C exhibits a brief but potent activation with respect to the erythropoietin receptor, MLP-H exhibits an activation that is weak yet lasts for a prolonged period of time, and therefore, the erythropoietin-derived peptide according to an aspect is capable of regulating activation of the erythropoietin receptor. Accordingly, the erythropoietin-derived peptide may be used as a therapeutic agent for conditions that require cell proliferative effects, such as anemia.

The invention claimed is:

1. A peptide consisting of the sequence of SEQ ID NO: 27.

2. The peptide of claim 1, wherein the peptide is derived from an erythropoietin protein sequence.

3. A composition for accelerating proliferation or differentiation of cells, comprising, as an active ingredient, the peptide of SEQ ID NO: 27.

4. The composition of claim 3, wherein the peptide binds to an erythropoietin receptor.

5. The composition of claim 3, wherein the peptide forms an alpha-helical structure.

6. The composition of claim 3, wherein the peptide has a cell protective activity.

7. The composition of claim 3, wherein the cells are hemocytoblasts, fat cells, pancreatic cells, muscle cells, blood vessel cells, or skin cells.

8. A pharmaceutical composition for treating an anemic disorder, comprising, as an active ingredient, the peptide of SEQ ID NO: 27.

9. The pharmaceutical composition of claim 8, wherein the composition accelerates proliferation of hemocytoblasts.

10. The pharmaceutical composition of claim 8, wherein the anemic disorder is selected from acute or chronic anemia, anemia associated with a kidney disorder, anemia associated with kidney failure, anemia associated with hemopathy, radiation therapy-induced anemia, chemotherapy-induced anemia, anemia associated with a surgical procedure, anemia associated with an infection, anemia associated with nutritional deficiency, abnormal erythropoiesis, initial anemia associated with premature birth, and a combination thereof.

* * * * *